United States Patent
Sato et al.

(10) Patent No.: US 6,184,319 B1
(45) Date of Patent: Feb. 6, 2001

(54) OLEFIN POLYMER, FILMS OR SHEETS MADE THEREFROM, AND PROCESS FOR THE PRODUCTION OF OLEFIN POLYMER

(75) Inventors: Hideki Sato, Niihama; Hiroaki Katayama; Kazuki Wakamatsu, both of Sodegaura; Hiroyuki Shiraishi, Ichihara, all of (JP)

(73) Assignee: Sumitomo Chemical Company, Limited, Osaka (JP)

( * ) Notice: Under 35 U.S.C. 154(b), the term of this patent shall be extended for 0 days.

(21) Appl. No.: 09/125,520

(22) PCT Filed: Dec. 19, 1997

(86) PCT No.: PCT/JP97/04713

§ 371 Date: Dec. 14, 1998

§ 102(e) Date: Dec. 14, 1998

(87) PCT Pub. No.: WO98/28342

PCT Pub. Date: Jul. 2, 1998

(30) Foreign Application Priority Data

Dec. 20, 1996 (JP) .................................................. 8/341988
Jan. 14, 1997 (JP) .................................................. 9/005033
Jan. 14, 1997 (JP) .................................................. 9/005034
Jul. 4, 1997 (JP) .................................................. 9/179693

(51) Int. Cl.$^7$ .................................................. C08F 4/44
(52) U.S. Cl. .................. 526/161; 526/348.5; 526/348.6; 526/351; 526/352; 502/117; 502/152
(58) Field of Search .................. 526/131, 161, 526/943, 348.6, 351, 352, 348.5

(56) References Cited

U.S. PATENT DOCUMENTS 5,084,534 * 1/1992 Welborn, Jr. et al. ................ 526/160

(List continued on next page.)

FOREIGN PATENT DOCUMENTS

0612769A1 * 8/1994 (EP) .

(List continued on next page.)

Primary Examiner—David W. Wu
Assistant Examiner—R. Harlan
(74) Attorney, Agent, or Firm—Birch, Stewart, Kolasch & Birch, LLP

(57) ABSTRACT

An olefin polymer characterized by having
(A) a density of from 0.850 to 0.940 g/cm$^3$,
(B) a melt flow rate (MFR) of from 0.1 to 200 g/10 minutes, and
(C) a relation between the melt flow rate (MFR) and an intrinsic viscosity [η] measured in tetralin at 135° C. satisfying the range of the following equation (1):

$$-4.04 \log [\eta]+0.6 \leq \log MFR \leq -4.04 \log [\eta]+0.96 \quad (1)$$

and its a film or sheet, and a method for producing an olefin polymer characterized by homopolymerizing an olefin or copolymerizing two or more olefins, with a catalyst for olefin polymerization, comprising:
(A) a transition metal complex represented by the general formula [I] below;
(B) at least one aluminum compound selected from (B1) to (B3); and/or
(C) at least one boron compound selected from (C1) to (C3), at a temperature of at least 130° C. under a pressure of at least 300 kg/cm$^2$G.

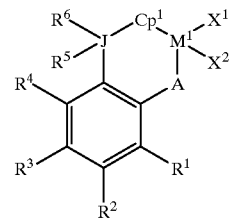

[I]

18 Claims, 2 Drawing Sheets

U.S. PATENT DOCUMENTS 5,218,071 * 6/1993 Tsutsui et al. .
5,272,236 * 12/1993 Lai et al. .
5,278,272 * 1/1994 Lai et al. .
5,408,017 * 4/1995 Turner et al. .
5,525,695 * 6/1996 Lai et al. .

FOREIGN PATENT DOCUMENTS

| 05842939A1 | * | 5/1998 | (EP) . |
| 0842939 | * | 5/1998 | (EP) . |
| 01503788 | * | 12/1989 | (JP) . |
| 07500622 | * | 1/1995 | (JP) . |
| 2571280B2 | * | 1/1997 | (JP) . |
| WO9514024 | * | 7/1995 | (WO) . |
| WO 9703992 | * | 6/1997 | (WO) . |

* cited by examiner

FIG.2

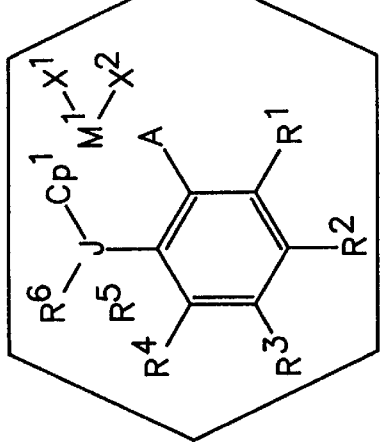

(A) Transition Metal Component

M¹:Group IV transition metal atom
A:Group XVI atom
J:Group XIV atom
$X^1$, $X^2$, $R^1$, $R^2$, $R^3$, $R^4$, $R^5$, and $R^6$ : hydrogen atom, halogen atom, alkyl group, aralkyl group, aryl group, substituted silyl group, alkoxy group, di-substituted amino group
$Cp^1$: group having a cyclopentadiene anion skeleton (B) Organometallic Component
Organoaluminum and/or aluminoxane (C) Third Component
Boron Compound Olefin (co)polymer Pressure of at least 300 kg/cm²G and temperature of at least 130°C

OLEFIN POLYMER, FILMS OR SHEETS MADE THEREFROM, AND PROCESS FOR THE PRODUCTION OF OLEFIN POLYMER This application is the national phase under 35 U.S.C. §371 of prior PCT International Application No. PCT/JP97/04713 which has an International filing date of Dec. 19, 1997 which designated the United States of America, the entire contents of which are hereby incorporated by reference.

TECHNICAL FIELD

The present invention relates to a novel olefin polymer, and a film or sheet of the olefin polymer. Furthermore, the present invention relates to a method for producing an olefin polymer using a catalyst for olefin polymerization, comprising a transition metal complex as one of the catalyst components. More particularly, the present invention relates to an olefin polymer having a good transparency and strength characteristics, a film or sheet of the olefin polymer, and a method for producing an olefin polymer with a catalyst for olefin polymerization, using a transition metal complex at high temperature under high pressure.

In the present invention, the olefin polymer includes a homopolymer of an olefin or a copolymer of two or more olefins.

BACKGROUND ART

An ionic polymerization method linear low-density polyethylene (LLDPE) as a copolymer of ethylene and an α-olefin has widely been used as a film, a sheet, a hollow container and a raw material for injection molding because of its excellent mechanical strength such as impact strength, tensile strength, and environmental stress-crack resistance, etc. However, when the above LLDPE is produced by using a solid catalyst, there arises a problem of tackiness of the molded article and it was not necessarily satisfactory. To solve the problem, LLDPE using a vanadium catalyst has been studied. However, there arises a problem of coloring due to a large amount of the catalyst residue in the polymer and it was not necessarily satisfactory. To solve those problems, various metallocene catalysts have recently been developed as a homogeneous catalyst.

As a method for industrially producing an olefin polymer at high temperature using a catalyst for olefin polymer, the following two methods are practiced at present. The first method is a method for polymerizing an olefin under the condition where a polymer is molten using a solvent such as cyclohexane, etc., which is generally referred to as a "high-temperature solution method", for example, a method for polymerizing an olefin under the condition of 120 to 250° C. and 5 to 50 kg/cm$^2$. The second method is a method for conducting polymerization in a state where the formed olefin polymer is molten in an olefin in a super critical fluid state at high temperature under high pressure in the absence of a solvent, which is generally referred to as a "high-pressure ionic polymerization method". These high-temperature solution polymerization method and high-pressure ionic polymerization method have advantages that a reactor is compact and replacement of a monomer can be easily performed.

For example, a method for obtaining an olefin polymer by using a metallocene catalyst under high pressure is disclosed in Japanese Patent Publication (Kohyo) No. Hei 1-503788, Japanese Patent Publication (Kokai) No. Hei 7-157508 and U.S. Pat. No. 5,408,017.

However, Japanese Patent Publication (Kohyo) No. Hei 1-503788 discloses a method for producing an olefin polymer by using a catalyst containing bis(n-butyl)cyclopentadienyl zirconium dichloride and methylaluminoxane in a high-pressure ionic polymerization method. Although the polymerization pressure is considerably high such as 1000 bar or more, the molecular weight of the resulting ethylene-α-olefin copolymer was insufficient. This method has an advantage such that an olefin polymer having a narrow molecular weight distribution and a composition distribution can be efficiently obtained and a film produced by using the olefin polymer has no feeling of tackiness, but the transparency of the film produced by using the resulting polymer is unsatisfactory.

Furthermore, Japanese Patent Publication (Kokai) No. Hei 7-157508 discloses a method for producing an olefin polymer with a catalyst obtained by using diphenylmethylene(cyclopentadienyl)(fluorenyl)zirconium dichloride, triisobutylaluminum and N,N-dimethylaniliniumtetrakis(pentafluorophenyl)borate in a high-pressure ionic polymerization method, and U.S. Pat. No. 5,408,017 discloses a method for producing an olefin polymer with a catalyst obtained by using dimethylsilylbis(4,5,6,7-tetrahydro-indenyl)zirconium dimethyl and N,N-dimethylaniliniumtetrakis (pentafluorophenyl)borate in a high-pressure ionic polymerization method. In these polymerization methods, although the polymerization pressure is high as not less than 900 kg/cm$^2$ and 1300 bar, respectively, the molecular weight of the ethylene-α-olefin copolymer obtained by any method was insufficient and the transparency of the film produced by using these polymers was unsatisfactory in the same manner as described above.

Japanese Patent No. 2571280 discloses an ethylene copolymer having a small Mw/Mn, narrow molecular weight, large MFR$_{10}$/MFR$_2$ and excellent fluidity, but the transparency and tear strength of the film produced by using this ethylene copolymer were not necessarily satisfactory.

Japanese Patent Publication (Kohyo) No. Hei 7-500622 discloses an olefin polymer wherein the melt flow ratio, Mw/Mn, shear stress at which a gross melt fracture arises, and number of melting points are specified, but the transparency and tear strength of the film produced by using this polymer were not necessarily satisfactory.

It is one of features that an olefin polymer having narrow molecular weight distribution and composition distribution is obtained by using a metallocene complex as a catalyst component, but there is a problem that control of density and polymerization activity, particularly a polymerization activity at the reaction temperature which is efficient for industrial production, are insufficient.

DISCLOSURE OF THE INVENTION

An object of the present invention is to provide an olefin polymer having good transparency and strength characteristics, and a film or sheet of the olefin polymer.

Another object of the present invention is to provide a method for efficiently producing an olefin polymer having narrow composition distribution, high molecular weight and arbitrary density under the conditions of high temperature and high pressure by using a highly active catalyst containing a novel metallocene complex.

Namely, according to the present invention, there is provided an olefin polymer characterized in that said olefin polymer has:

(A) a density of from 0.850 to 0.940 g/cm$^3$;

(B) a melt flow rate (MFR) is from 0.1 to 200 g/10 minutes; and (C) a relation between the melt flow rate (MFR) and an intrinsic viscosity [η] measured in tetralin at 135° C. satisfying the range of the following equation 1:

$$-4.04 \log [\eta]+0.6 \leq \log MFR \leq 4.04 \log [\eta]+0.96 \quad \text{equation 1}$$

The present invention also provides a film or sheet characterized by being made from the above olefin polymer.

Furthermore, according to the present invention, there is provided a method for producing an olefin polymer, which comprises homopolymerizing an olefin or copolymerizing two or more olefins at a temperature of at least 130° C. under a pressure of at least 300 kg/cm²G with a catalyst for olefin polymerization, comprising the following (A), (B) and (C); (A) and (B); or (A) and (C):

(A): a transition metal complex represented by the following general formula [I]:

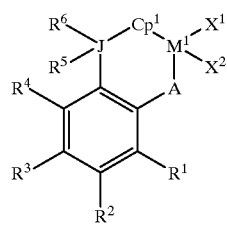

(wherein $M^1$ represents a transition metal atom of Group IV of the Periodic Table of the Elements; A represents an atom of Group XVI of the Periodic Table of the Elements; J represents an atom of Group XIV of the Periodic Table of the Elements; $Cp^1$ represents a group having a cyclopentadiene type anion skeleton; $X^1$, $X^2$, $R^1$, $R^2$, $R^3$, $R^4$, $R^5$ and $R^6$ independently represent a hydrogen atom, a halogen atom, an alkyl group, an aralkyl group, an aryl group, a substituted silyl group, an alkoxy group, an aralkyloxy group, an aryloxy group or a di-substituted amino group; and $R^1$, $R^2$, $R^3$, $R^4$, $R^5$ and $R^6$ may be optionally combined with each other to form a ring);

(B): at least one aluminum compound selected from the following (B1) to (B3)

(B1) an organoaluminum compound represented by the general formula $E^1_a AlZ_{3-a}$, (B2) a cyclic aluminoxane having a structure represented by the general formula $\{-Al(E^2)-O-\}_b$, and (B3) a linear aluminoxane having a structure represented by the general formula $E^3\{-Al(E^3)-O-\}_c AlE^3_2$ (wherein $E^1$, $E^2$ and $E^3$ respectively represents a hydrocarbon group, all of $E^1$, $E^2$ and $E^3$ may be the same or different; Z represents a hydrogen atom or a halogen atom, and all of Z may be the same or different; a represents a numeral of 0 to 3; b represents an integer of not less than 2; and c represents an integer of not less than 1); and (C): a boron compound of any one of the following (C1) to (C3);

(C1) a boron compound represented by the general formula $BQ^1Q^2Q^3$, (C2) a boron compound represented by the general formula $G^+(BQ^1Q^2Q^3Q^4)^-$, and (C3) a boron compound represented by the general formula $(L-H)^+(BQ^1Q^2Q^3Q^4)^-$ (wherein B represents a boron atom in the trivalent valence state; $Q^1$ to $Q^4$ may be the same or different and represent a halogen atom, a hydrocarbon group, a halogenated hydrocarbon group, a substituted silyl group, an alkoxy group or a di-substituted amino group; G+ represents an inorganic or organic cation; L represents a neutral Lewis base; and (L—H)+ represents a Brønsted acid).

The present invention will be described in detail hereinafter.

The olefin polymer of the present invention has a density of 0.850 to 0.940 g/cm³, preferably 0.880 to 0.935 g/cm³, more preferably 0.900 to 0.935 g/cm³. When the density is too low, a film or sheet having high tackiness is obtained. On the other hand, when the density is too high, the effect of the transparency disappears.

The melt flow rate (MFR) (JIS K-6760, 190° C., load of 2.16 kg) of the olefin polymer is from 0.1 to 200 g/10 minutes, preferably from 0.2 to 20 g/10 minutes. When the melt flow rate is too low, the load during the molding of the film and sheet is large. On the other hand, when the melt flow rate is too high, the strength of the film or sheet is lowered.

The olefin polymer of the present invention is an olefin polymer wherein a relation between the melt flow rate (MFR) and an intrinsic viscosity [η] measured in tetralin at 135° C. satisfies the condition of the following equation 1, preferably the following equation 2. In case of the following equation 3 which does not satisfy the following equation 2, a balance between the transparency and strength characteristics, particularly tear strength, becomes poor. In case of the following equation 4, the transparency becomes poor.

$$-4.04 \log [\eta]+0.6 \leq \log MFR \leq -4.04 \log [\eta]+0.96 \quad \text{equation 1}$$

$$-4.04 \log [\eta]+0.76 \leq \log MFR \leq -4.04 \log [\eta]+0.96 \quad \text{equation 2}$$

$$-4.04 \log [\eta]+0.6 > \log MFR \quad \text{equation 3}$$

$$\log MFR > -4.04 \log [\eta]+0.96 \quad \text{equation 4}$$

Regarding the olefin polymer of the present invention, the ratio Q (Mw/Mn) of a weight-average molecular weight (Mw) to a number-average molecular weight (Mn) as an index of a molecular weight distribution of the polymer is preferably not more than 5, more preferably 2 to 4.

The olefin polymer of the present invention can be produced with a catalyst for olefin polymerization, comprising the following compounds (A) and (B), (A) and (C), or (A), (B) and (C).

Compound (A): a complex of a transition metal having a cyclopentadiene anion skeleton, of Group IV of the Periodic Table of the Elements Compound (B): at least one aluminum compound selected from the following (B1) to (B3):

(B1) an organoaluminum compound represented by the general formula $E^1_a AlZ_{3-a}$;

(B2) a cyclic aluminoxane having a structure represented by the general formula $\{-Al(E^2)-O-\}_b$; and (B3) a linear aluminoxane having a structure represented by the general formula $E^3\{-Al(E^3)-O-\}_c AlE^3_2$ (wherein $E^1$, $E^2$ and $E^3$ respectively represents a hydrocarbon group, all of $E^1$, $E^2$ and $E^3$ may be the same or different; Z represents a hydrogen atom or a halogen atom, and all of Z may be the same or different; a represents a numeral satisfying $0 < a \leq 3$; b represents an integer of not less than 2; and c represents an integer of not less than 1), and Compound (C): a boron compound of any one of the following (C1) to (C3):

(C1) a boron compound represented by the general formula $BQ^1Q^2Q^3$;

(C2) a boron compound represented by the general formula $G^+(BQ^1Q^2Q^3Q^4)^-$; and (C3) a boron compound represented by the general formula $(L-H)^+(BQ^1Q^2Q^3Q^4)^-$ (wherein B represents a boron atom in the trivalent valence state; $Q^1$ to $Q^4$ may be the same or different and represent a halogen atom, a hydrocarbon group, a halogenated hydrocarbon group, a substituted silyl group, an alkoxy group or a di-substituted amino group; $G^+$ represents an inorganic or organic cation; L represents a neutral Lewis base; and $(L-H)^+$ represents a Brønsted acid).

(A) Transition Metal Compound

It is a complex of a transition metal having a cyclopentadiene type anion skeleton, of Group IV of the Periodic Table of the Elements, and specific examples thereof include compounds described in the following (a) to (c):

(a) Complex compound represented by the following general formula [II]:

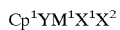

$$Cp^1YM^1X^1X^2 \quad \quad [II]$$

(b) Complex compound described in Japanese Patent Publication (Kokai) No. Hei 3-163088

Specific examples of (b) include (tert-butylamide)(tetramethyl-$\eta^5$-cyclopentadienyl)-1,2-ethanediyl zirconium dichloride, (tert-butylamide)(tetramethyl-$\eta^5$-cyclopentadienyl)-1,2-ethanediyl titanium dichloride, (methylamide)(tetramethyl-$\eta^5$-cyclopentadienyl)-1,2-ethanediyl zirconium dichloride, (methylamide)(tetramethyl-$\eta^5$-cyclopentadienyl)-1,2-ethanediyl titanium dichloride, (tert-butylamide)dimethyl(tetramethyl-$\eta^5$-cyclopentadienyl)silane zirconium dichloride, (tert-butylamide)dimethyl(tetramethyl-$\eta^5$-cyclopentadienyl)silane titanium dichloride, etc.

(c) Complex compound represented by the general formula [I]:

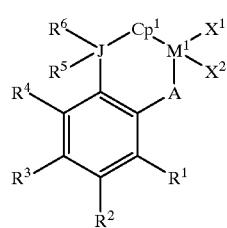

(in the above formulas [I] and [II], $M^1$ represents a transition metal atom of Group IV of the Periodic Table of the elements; A represents an atom of Group XVI of the Periodic Table of the Elements; J represents an atom of Group XIV of the Periodic Table of the elements; $Cp^1$ represents a group having a cyclopentadiene anion skeleton; $X^1$, $X^2$, $R^1$, $R^2$, $R^3$, $R^4$, $R^5$ and $R^6$ independently represent a hydrogen atom, a halogen atom, an alkyl group, an aralkyl group, an aryl group, a substituted silyl group, an alkoxy group, an aralkyloxy group, an aryloxy group or a di-substituted amino group, and $R^1$, $R^2$, $R^3$, $R^4$, $R^5$ and $R^6$ may be optionally combined with each other to form a ring; and Y represents a ligand, which contains nitrogen, phosphorous, oxygen or sulfur and has up to 20 atoms other than hydrogen atom).

Among the above (a) to (c), (c) is particularly preferred in view of the molecular weight required for formation of the film and sheet as well as transparency of the film and sheet.

The above (a) and (c) will be described in detail hereinafter.

In the general formulas [I] and [II], the transition metal atom represented by $M^1$ means a transition metal element of Group IV of the Periodic Table of the Elements (IUPAC Inorganic Chemistry Nomenclature, Revised Edition, 1989), and examples thereof include titanium atom, zirconium atom, hafnium atom, etc. Among them, titanium atom or zirconium atom is preferred.

The group having a cyclopentadiene anion skeleton, as for the substituent $Cp^1$, includes $\eta^5$-(substituted) cyclopentadienyl group, $\eta^5$-(substituted)indenyl group, $\eta^5$-(substituted)fluorenyl group, etc. Specific examples thereof include $\eta^5$-cyclopentadienyl group, $\eta^5$-methylcyclopentadienyl group, $\eta^5$-dimethylcyclopentadienyl group, $\eta^5$-trimethylcyclopentadienyl group, $\eta^5$-tetramethylcyclopentadienyl group, $\eta^5$-ethylcyclopentadienyl group, $\eta^5$-n-propylcyclopentadienyl group, $\eta^5$-isopropylcyclopentadienyl group, $\eta^5$-n-butylcyclopentadienyl group, $\eta^5$-sec-butylcyclopentadienyl group, $\eta^5$-tert-butylcyclopentadienyl group, $\eta^5$-n-pentylcyclopentadienyl group, $\eta^5$-neopentylcyclopentadienyl group, $\eta^5$-n-hexylcyclopentadienyl group, $\eta^5$-n-octylcyclopentadienyl group, $\eta^5$-phenylcyclopentadienyl group, $\eta^5$-naphthylcyclopentadienyl group, $\eta^5$-trimethylsilylcyclopentadienyl group, $\eta^5$-triethylsilylcyclopentadienyl group, $\eta^5$-tert-butyldimethylsilylcyclopentadienyl group, $\eta^5$-indenyl group, $\eta^5$-methylindenyl group, $\eta^5$-dimethylindenyl group, $\eta^5$-ethylindenyl group, $\eta^5$-n-propylindenyl group, $\eta^5$-isopropylindenyl group, $\eta^5$-n-butylindenyl group, $\eta^5$-sec-butylindenyl group, $\eta^5$-tert-butylindenyl group, $\eta^5$-n-pentylindenyl group, $\eta^5$-neopentylindenyl group, $\eta^5$-n-hexylindenyl group, $\eta^5$-n-octylindenyl group, $\eta^5$-n-decylindenyl group, $\eta^5$-phenylindenyl group, $\eta^5$-methylphenylindenyl group, $\eta^5$-naphthylindenyl group, $\eta^5$-trimethylsilylindenyl group, $\eta^5$-triethylsilylindenyl group, $\eta^5$-tert-butyldimethylsilylindenyl group, $\eta^5$-tetrahydroindenyl group, $\eta^5$-fluorenyl group, $\eta^5$-methylfluorenyl group, $\eta^5$-dimethylfluorenyl group, $\eta^5$-ethylfluorenyl group, $\eta^5$-diethylfluorenyl group, $\eta^5$-n-propylfluorenyl group, $\eta^5$-di-n-propylfluorenyl group, $\eta^5$-isopropylfluorenyl group, $\eta^5$-diisopropylfluorenyl group, $\eta^5$-n-butylfluorenyl group, $\eta^5$-sec-butylfluorenyl group, $\eta^5$-tert-butylfluorenyl group, $\eta^5$-di-n-butylfluorenyl group, $\eta^5$-di-sec-butylfluorenyl group, $\eta^5$-di-tert-butylfluorenyl group, $\eta^5$-n-pentylfluorenyl group, $\eta^5$-neopentylfluorenyl group, $\eta^5$-n-hexylfluorenyl group, $\eta^5$-n-octylfluorenyl group, $\eta^5$-n-decylfluorenyl group, $\eta^5$-n-dodecylfluorenyl group, $\eta^5$-phenylfluorenyl group, $\eta^5$-diphenylfluorenyl group, $\eta^5$-methylphenylfluorenyl group, $\eta^5$-naphthylfluorenyl group, $\eta^5$-trimethylsilylfluorenyl group, $\eta^5$-bis-trimethylsilylfluorenyl group, $\eta^5$-triethylsilylfluorenyl group, $\eta^5$-tert-butyldimethylsilylfluorenyl group, etc. Among them, $\eta^5$-cyclopentadienyl group, $\eta^5$-methylcyclopentadienyl group, η⁵-tert-butylcyclopentadienyl group, η⁵-tetramethylcyclopentadienyl group, η⁵-indenyl group or η⁵-fluorenyl group is particularly preferred.

In the general formula [II], Y is a ligand, which contains nitrogen, phosphorous, oxygen or sulfur and has up to 20 atoms other than hydrogen atom.

Examples of the atom of Group XVI of the Periodic Table of the Elements as for A in the general formula [I] include oxygen atom, sulfur atom, selenium atom, etc., preferably oxygen atom.

Examples of the atom of Group XIV of the Periodic Table of the Elements as for J in the general formula [I] include carbon atom, silicon atom, germanium atom, etc., preferably carbon atom or silicon atom.

Examples of the halogen atom in the substituent $X^1$, $X^2$, $R^1$, $R^2$, $R^3$, $R^4$, $R^5$ or $R^6$ include fluorine atom, chlorine atom, bromine atom and iodine atom, preferably chlorine atom or bromine atom, more preferably chlorine atom.

As the alkyl group in the substituent $X^1$, $X^2$, $R^1$, $R^2$, $R^3$, $R^4$, $R^5$ or $R^6$, an alkyl group having 1 to 20 carbon atoms is preferred. Examples thereof include methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group, n-eicosyl group, etc., more preferably methyl group, ethyl group, isopropyl group, tert-butyl group or amyl group.

All of these alkyl groups may be substituted with a halogen atom (fluorine atom, chlorine atom, bromine atom or iodine atom). Examples of the alkyl group having 1 to 20 carbon atoms, which is substituted with the halogen atom, include fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, perbromoeicosyl group, etc.

All of these alkyl groups may be partially substituted with an alkoxy group such as methoxy group, ethoxy group, etc., an aryloxy group such as phenoxy group, etc. or an aralkyloxy group such as benzyloxy group, etc.

As the aralkyl group in the substituent $X^1$, $X^2$, $R^1$, $R^2$, $R^3$, $R^4$, $R^5$ or $R^6$, an aralkyl group having 7 to 20 carbon atoms is preferred. Examples thereof include benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (3,5-dimethylphenyl)methyl group, (4,6-dimethylphenyl)methyl group, (2,3,4-timethylphenyl)methyl group, (2,3,5-timethylphenyl)methyl group, (2,3,6-timethylphenyl)methyl group, (3,4,5-timethylphenyl)methyl group, (2,4,6-timethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-dodecylphenyl)methyl group, (n-tetradecylphenyl)methyl group, naphthylmethyl group, anthracenylmethyl group, etc., more preferably benzyl group.

All of these aralkyl groups may be partially substituted with a halogen atom (fluorine atom, chlorine atom, bromine atom or iodine atom), an alkoxy group such as methoxy group, ethoxy group, etc., an aryloxy group such as phenoxy group, etc. or an aralkyloxy group such as benzyloxy group, etc.

As the aryl group in the substituent $X^1$, $X^2$, $R^1$, $R^2$, $R^3$, $R^4$, $R^5$ or $R^6$, an aryl group having 6 to 20 carbon atoms is preferred. Examples thereof include phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, naphthyl group, anthracenyl group, etc., more preferably phenyl group.

All of these aryl groups may be partially substituted with a halogen atom (fluorine atom, chlorine atom, bromine atom or iodine atom), an alkoxy group such as methoxy group, ethoxy group, etc., an aryloxy group such as phenoxy group, etc. or an aralkyloxy group such as benzyloxy group, etc.

The substituted silyl group in the substituent $X^1$, $X^2$, $R^1$, $R^2$, $R^3$, $R^4$, $R^5$ or $R^6$ is a silyl group substituted with a hydrocarbon group, and examples of the hydrocarbon group include an alkyl group having 1 to 10 carbon atoms, such as methyl group, ethyl group, n-propyl group, isopropyl group, n-butyl group, sec-butyl group, tert-butyl group, isobutyl group, n-pentyl group, n-hexyl group, cyclohexyl group, etc., and an aryl group such as phenyl group. Examples of the substituted silyl group having 1 to 20 carbon atoms include mono-substituted silyl group having 1 to 20 carbon atoms, such as methylsilyl group, ethylsilyl group, phenylsilyl group, etc.; di-substituted silyl group having 2 to 20 carbon atoms, such as dimethylsilyl group, diethylsilyl group, diphenylsilyl group, etc.; and tri-substituted silyl group having 3 to 20 carbon atoms, such as trimethylsilyl group, triethylsilyl group, tri-n-propylsilyl group, triisopropylsilyl group, tri-n-butylsilyl group, tri-sec-butylsilyl group, tri-tert-butylsilyl group, tri-isobutylsilyl group, tert-butyl-dimethylsilyl group, tri-n-pentylsilyl group, tri-n-hexylsilyl group, tricyclohexylsilyl group, triphenylsilyl group, etc., preferably trimethylsilyl group, tert-butyldimethylsilyl group or triphenylsilyl group.

All of the hydrocarbon groups of these substituted silyl groups may be partially substituted with a halogen atom (fluorine atom, chlorine atom, bromine atom or iodine atom), an alkoxy group such as methoxy group, ethoxy group, etc., an aryloxy group such as phenoxy group, etc. or an aralkyloxy group such as benzyloxy group, etc.

As the alkoxy group in the substituent $X^1$, $X^2$, $R^1$, $R^2$, $R^3$, $R^4$, $R^5$ or $R^6$, an alkoxy group having 1 to 20 carbon atoms is preferred. Examples thereof include methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dodecoxy group, n-pentadecoxy group, n-eicosoxy group, etc., more preferably methoxy group, ethoxy group or tert-butoxy group.

All of these alkoxy groups may be partially substituted with a halogen atom (fluorine atom, chlorine atom, bromine atom or iodine atom), an alkoxy group such as methoxy group, ethoxy group, etc., an aryloxy group such as phenoxy group, etc. or an aralkyloxy group such as benzyloxy group, etc.

As the aralkyloxy group in the substituent $X^1$, $X^2$, $R^1$, $R^2$, $R^3$, $R^4$, $R^5$ or $R^6$, an aralkyloxy group having 7 to 20 carbon atoms is preferred. Examples thereof include benzyloxy group, (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (3,5-dimethylphenyl)methoxy group, (2,3,4-trimethylphenyl)methoxy group, (2,3,5-trimethylphenyl)methoxy group, (2,3,6-trimethylphenyl)methoxy group, (2,4,5-trimethylphenyl)methoxy group, (2,4,6-trimethylphenyl)methoxy group, (3,4,5-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-hexylphenyl)methoxy group, (n-octylphenyl)methoxy group, (n-decylphenyl)methoxy group, (n-tetradecylphenyl)methoxy group, naphthylmethoxy group, anthracenyl-methoxy group, etc., more preferably benzyloxy group.

All of these aralkyloxy groups may be partially substituted with a halogen atom (fluorine atom, chlorine atom, bromine atom or iodine atom), an alkoxy group such as methoxy group, ethoxy group, etc., an aryloxy group such as phenoxy group, etc. or an aralkyloxy group such as benzyloxy group, etc.

As the aryloxy group in the substituent $X^1$, $X^2$, $R^1$, $R^2$, $R^3$, $R^4$, $R^5$ or $R^6$, an aralkyloxy group having 6 to 20 carbon atoms is preferred. Examples thereof include phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-triethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, naphthoxy group, anthracenoxy group, etc.

All of these aryloxy groups may be partially substituted with a halogen atom (fluorine atom, chlorine atom, bromine atom or iodine atom), an alkoxy group such as methoxy group, ethoxy group, etc., an aryloxy group such as phenoxy group, etc. or an aralkyloxy group such as benzyloxy group, etc.

The di-substituted amino group in the substituent $X^1$, $X^2$, $R^1$, $R^2$, $R^3$, $R^4$, $R^5$ or $R^6$ is an amino group substituted with two hydrocarbon groups, and examples of the hydrocarbon group include alkyl group having 1 to 10 carbon atoms, such as methyl group, ethyl group, n-propyl group, isopropyl group, n-butyl group, sec-butyl group, tert-butyl group, isobutyl group, n-pentyl group, n-hexyl group, cyclohexyl group, etc.; aryl group having 6 to 10 carbon atoms, such as phenyl group, etc.; and aralkyl group having 7 to 10 carbon atoms. Examples of the di-substituted amino group substituted with the hydrocarbon group having 1 to 10 carbon atoms include dimethylamino group, diethylamino group, di-n-propylamino group, diisopropylamino group, di-n-butylamino group, di-sec-butylamino group, di-tert-butylamino group, di-isobutylamino group, tert-butylisopropylamino group, di-n-hexylamino group, di-n-octylamino group, di-n-decylamino group, diphenylamino group, bistrimethylsilylamino group, bis-tert-butyldimethylsilylamino group, etc., preferably dimethylamino group or diethylamino group.

The substituent $R^1$, $R^2$, $R^3$, $R^4$, $R^5$ and $R^6$ may be optionally combined with each other to form a ring.

$R^1$ is preferably an alkyl group, an aralkyl group, an aryl group or a substituted silyl group.

Preferably, each of $X^1$ and $X^2$ is independently a halogen atom, an alkyl group, an aralkyl group, an alkoxy group, an aryloxy group or a di-substituted amino group, more preferably halogen atom.

Examples of the compound A represented by the formula [I] (hereinafter referred to as a "transition metal complex A", sometimes) include transition metal complex wherein J is a carbon atom in the general formula [I], such as methylene(cyclopentadienyl)(3,5-dimethyl-2-phenoxy)titanium dichloride, methylene(cyclopentadienyl)(3-tert-butyl-2-phenoxy)titanium dichloride, methylene(cyclopentadienyl)(3-tert-butyl-5-methyl-2-phenoxy)titanium dichloride, methylene(cyclopentadienyl)(3-phenyl-2-phenoxy)titanium dichloride, methylene(cyclopentadienyl)(3-tert-butyldimethylsilyl-5-methyl-2-phenoxy)titanium dichloride, methylene(cyclopentadienyl)(3-trimethylsilyl-5-methyl-2-phenoxy)titanium dichloride, methylene(cyclopentadienyl)(3-tert-butyl-5-methoxy-2-phenoxy)titanium dichloride, ethylene(cyclopentadienyl)(3-tert-butyl-5-chloro-2-phenoxy)titanium dichloride, methylene(methylcyclopentadienyl)(3,5-dimethyl-2-phenoxy)titanium dichloride, methylene(methylcyclopentadienyl)(3-tert-butyl-2-phenoxy)titanium dichloride, methylene(methylcyclopentadienyl)(3-tert-butyl-5-methyl-2-phenoxy)titanium dichloride, methylene(methylcyclopentadienyl)(3-phenyl-2-phenoxy)titanium dichloride, methylene(methylcyclopentadienyl)(3-tert-butyldimethylsilyl-5-methyl-2-phenoxy)titanium dichloride, methylene(methylcyclopentadienyl)(3-trimethylsilyl-5-methyl-2-phenoxy)titanium dichloride, methylene(methylcyclopentadienyl)(3-tert-butyl-5-methoxy-2-phenoxy)titanium dichloride, methylene(methylcyclopentadienyl)(3-tert-butyl-5-chloro-2-phenoxy)titanium dichloride, methylene(tert-butylcyclopentadienyl)(3,5-dimethyl-2-phenoxy)titanium dichloride, methylene(tert-butylcyclopentadienyl)(3-tert-butyl-2-phenoxy)titanium dichloride, methylene(tert-butylcyclopentadienyl)

(3-tert-butyl-5-methyl-2-phenoxy)titanium dichloride, methylene(tert-butylcyclopentadienyl)(3-phenyl-2-phenoxy)titanium dichloride, methylene(tert-butylcyclopentadienyl)(3-tert-butyldimethylsilyl-5-methyl-2-phenoxy)titanium dichloride, methylene(tert-butylcyclopentadienyl)(3-trimethylsilyl-5-methyl-2-phenoxy)titanium dichloride, methylene(tert-butylcyclopentadienyl)(3-tert-butyl-5-methoxy-2-phenoxy)titanium dichloride, methylene(tert-butylcyclopentadienyl)(3-tert-butyl-5-chloro-2-phenoxy)titanium dichloride, methylene(tetramethylcyclopentadienyl)(3,5-dimethyl-2-phenoxy)titanium dichloride, methylene(tetramethylcyclopentadienyl)(3-tert-butyl-2-phenoxy)titanium dichloride, methylene(tetramethylcyclopentadienyl)(3-tert-butyl-5-methyl-2-phenoxy)titanium dichloride, methylene(tetramethylcyclopentadienyl)(3-phenyl-2-phenoxy)titanium dichloride, methylene(tetramethylcyclopentadienyl)(3-tert-butyldimethylsilyl-5-methyl-2-phenoxy)titanium dichloride, methylene(tetramethylcyclopentadienyl)(3-trimethylsilyl-5-methyl-2-phenoxy)titanium dichloride, methylene(tetramethylcyclopentadienyl)(3-tert-butyl-5-methoxy-2-phenoxy)titanium dichloride, methylene(tetramethylcyclopentadienyl)(3-tert-butyl-5-chloro-2-phenoxy)titanium dichloride, methylene(trimethylsilylcyclopentadienyl)(3,5-dimethyl-2-phenoxy)titanium dichloride, methylene(trimethylsilylcyclopentadienyl)(3-tert-butyl-2-phenoxy)titanium dichloride, methylene(trimethylsilylcyclopentadienyl)(3-tert-butyl-5-methyl-2-phenoxy)titanium dichloride, methylene(trimethylsilylcyclopentadienyl)(3-phenyl- 2-phenoxy)titanium dichloride, methylene(trimethylsilylcyclopentadienyl)(3-tert-butyldimethylsilyl-5-methyl-2-phenoxy)titanium dichloride, methylene(trimethylsilylcyclopentadienyl)(3-trimethylsilyl-5-methyl-2-phenoxy)titanium dichloride, methylene(trimethylsilylcyclopentadienyl)(3-tert-butyl-5-methoxy-2-phenoxy)titanium dichloride, methylene(trimethylsilylcyclopentadienyl)(3-tert-butyl-5-chloro-2-phenoxy)titanium dichloride, methylene(fluorenyl)(3,5-dimethyl-2-phenoxy)titanium dichloride, methylene(fluorenyl)(3-tert-butyl-2-phenoxy)titanium dichloride, methylene(fluorenyl)(3-tert-butyl-5-methyl-2-phenoxy)titanium dichloride, methylene(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy)titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl- 2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene(methylcyclopentadienyl)(3-tert-butyldimethylsilyl-5-methyl-2-phenoxy)titanium dichloride, isopropylidene(methylcyclopentadienyl)(3-trimethylsilyl-5-methyl-2-phenoxy)titanium dichloride, isopropylidene(methylcyclopentadienyl)(3-tert-butyl-5-methoxy-2-phenoxy)titanium dichloride, isopropylidene(methylcyclopentadienyl)(3-tert-butyl-5-chloro-2-phenoxy)titanium dichloride, isopropylidene(tert-butylcyclopentadienyl)(3,5-dimethyl-2-phenoxy)titanium dichloride, isopropylidene(tert-butylcyclopentadienyl)(3-tert-butyl-2-phenoxy)titanium dichloride, isopropylidene(tert-butylcyclopentadienyl)(3-tert-butyl-5-methyl-2-phenoxy)titanium dichloride, isopropylidene(tert-butylcyclopentadienyl)(3-phenyl-2-phenoxy)titanium dichloride, isopropylidene(tert-butylcyclopentadienyl)(3-tert-butyldimethylsilyl-5-methyl-2-phenoxy)titanium dichloride, isopropylidene(tert-butylcyclopentadienyl)(3-trimethylsilyl-5-methyl-2-phenoxy)titanium dichloride, isopropylidene(tert-butylcyclopentadienyl)(3-tert-butyl-5-methoxy-2-phenoxy)titanium dichloride, isopropylidene(tert-butylcyclopentadienyl)(3-tert-butyl-5-chloro-2-phenoxy)titanium dichloride, isopropylidene(tetramethylcyclopentadienyl)(3,5-dimethyl-2-phenoxy)titanium dichloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5-methyl-2-phenoxy)titanium dichloride, isopropylidene(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy)titanium dichloride, isopropylidene(tetramethylcyclopentadienyl)(3-tert-butyl-5-chloro-2-phenoxy)titanium dichloride, isopropylidene(trimethylsilylcyclopentadienyl)(3,5-dimethyl-2-phenoxy)titanium dichloride, isopropylidene(trimethylsilylcyclopentadienyl)(3-tert-butyl-2-phenoxy)titanium dichloride, isopropylidene(trimethylsilylcyclopentadienyl)(3-tert-butyl-5-methyl-2-phenoxy)titanium dichloride, isopropylidene(trimethylsilylcyclopentadienyl)(3-phenyl-2-phenoxy)titanium dichloride, isopropylidene(trimethylsilylcyclopentadienyl)(3-tert-butyldimethylsilyl-5-methyl-2-phenoxy)titanium dichloride, isopropylidene(trimethylsilylcyclopentadienyl)(3-trimethylsilyl-5-methyl-2-phenoxy)titanium dichloride, isopropylidene(trimethylsilylcyclopentadienyl)(3-tert-butyl-5-methoxy-2-phenoxy)titanium dichloride, isopropylidene(trimethylsilylcyclopentadienyl)(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl-2-phenoxy)titanium dichloride, isopropylidene(fluorenyl)(3-tert-butyl-5-methyl-2-phenoxy)titanium dichloride, isopropylidene(fluorenyl)(3-phenyl-2-phenoxy)titanium dichloride, isopropylidene(fluorenyl)(3-tert-butyldimethylsilyl-5-methyl-2-phenoxy)titanium dichloride, isopropylidene(fluorenyl)(3- trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy)titanium dichloride, diphenylmethylene(cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyldimethylsilyl-5-methyl-2-phenoxy)titanium dichloride, diphenylmethylene(methylcyclopentadienyl)(3-trimethylsilyl-5-methyl-2-phenoxy)titanium dichloride, diphenylmethylene(methylcyclopentadienyl)(3-tert-butyl-5-methoxy-2-phenoxy)titanium dichloride, diphenylmethylene(methylcyclopentadienyl)(3-tert-butyl-5-chloro-2-phenoxy)titanium dichloride, diphenylmethylene(tert-butylcyclopentadienyl)(3,5-dimethyl-2-phenoxy)titanium dichloride, diphenylmethylene(tert-butylcyclopentadienyl)(3-tert-butyl-2-phenoxy)titanium dichloride, diphenylmethylene(tert-butylcyclopentadienyl)(3-tert-butyl-5-methyl-2-phenoxy)titanium dichloride, diphenylmethylene(tert-butylcyclopentadienyl)(3-phenyl-2-phenoxy)titanium dichloride, diphenylmethylene(tert-butylcyclopentadienyl)(3-tert-butyldimethylsilyl-5-methyl-2-phenoxy)titanium dichloride, diphenylmethylene(tert-butylcyclopentadienyl)(3-trimethylsilyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene(tert-butylcyclopentadienyl)(3-tert-butyl-5-chloro-2-phenoxy)titanium dichloride, diphenylmethylene(tetramethylcyclopentadienyl)(3,5-dimethyl-2-phenoxy)titanium dichloride, diphenylmethylene(tetramethylcyclopentadienyl)(3-tert-butyl-2-phenoxy)titanium dichloride, diphenylmethylene(tetramethylcyclopentadienyl)(3-tert-butyl-5-methyl-2-phenoxy)titanium dichloride, diphenylmethylene(tetramethylcyclopentadienyl)(3-phenyl-2-phenoxy)titanium dichloride, diphenylmethylene(tetramethylcyclopentadienyl)(3-tert-butyldimethylsilyl-5-methyl-2-phenoxy)titanium dichloride, diphenylmethylene(tetramethylcyclopentadienyl)(3-trimethylsilyl-5-methyl-2-phenoxy)titanium dichloride, diphenylmethylene(tetramethylcyclopentadienyl)(3-tert-butyl-5-methoxy-2-phenoxy)titanium dichloride, diphenylmethylene(tetramethylcyclopentadienyl)(3-tert-butyl-5-chloro-2-phenoxy)titanium dichloride, diphenylmethylene(trimethylsilylcyclopentadienyl)(3,5-dimethyl-2-phenoxy)titanium dichloride, diphenylmethylene(trimethylsilylcyclopentadienyl)(3-tert-butyl-2-phenoxy)titanium dichloride, diphenylmethylene(trimethylsilylcyclopentadienyl)(3-tert-butyl-5-methyl-2-phenoxy)titanium dichloride, diphenylmethylene(trimethylsilylcyclopentadienyl)(3-phenyl-2-phenoxy)titanium dichloride, diphenylmethylene(trimethylsilylcyclopentadienyl)(3-tert-butyldimethylsilyl-5-methyl-2-phenoxy)titanium dichloride, diphenylmethylene(trimethylsilylcyclopentadienyl)(3-trimethylsilyl-5-methyl-2-phenoxy)titanium dichloride, diphenylmethylene(trimethylsilylcyclopentadienyl)(3-tert-butyl-5-methoxy-2-phenoxy)titanium dichloride, diphenylmethylene(trimethylsilylcyclopentadienyl)(3-tert-butyl-5-chloro-2-phenoxy)titanium dichloride, diphenylmethylene(fluorenyl)(3,5-dimethyl-2-phenoxy)titanium dichloride, diphenylmethylene(fluorenyl)(3-tert-butyl-2-phenoxy)titanium dichloride, diphenylmethylene(fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride, diphenylmethylene(fluorenyl)(3-tert-butyl-5-chloro-2-phenoxy) titanium dichloride, compounds wherein titanium of these compounds is replaced by zirconium or hafnium, compounds wherein dichloride of these compounds is replaced by dibromide, diiodide, bis(dimethylamide), bis(diethylamide), di-n-butoxide or diisopropoxide, compounds wherein (cyclopentadienyl) of these compounds is replaced by (dimethylcyclopentadienyl), (trimethylcyclopentadienyl), (n-butylcyclopentadienyl), (tert-butyldimethylsilylcyclopentadienyl) or (indenyl), and compounds wherein (3,5-dimethyl-2-phenoxy) of these compounds is replaced by (2-phenoxy), (3-methyl-2-phenoxy), (3,5-di-tert-butyl-2-phenoxy), (3-phenyl-5-methyl-2-phenoxy), (3-tert-butyldimethylsilyl-2-phenoxy) or (3-trimethylsilyl-2-phenoxy); and transition metal complex wherein J is an atom of Group XIV of the Periodic Table of the Elements other than carbon atom, such as dimethylsilyl(cyclopentadienyl)(2-phenoxy)titanium dichloride, dimethylsilyl(cyclopentadienyl)(3-methyl-2-phenoxy)titanium dichloride, dimethylsilyl(cyclopentadienyl)(3,5-dimethyl-2-phenoxy)titanium dichloride, dimethylsilyl(cyclopentadienyl)(3-tert-butyl-2-phenoxy)titanium dichloride, dimethylsilyl(cyclopentadienyl)(3-tert-butyl-5-methyl-2-phenoxy)titanium dichloride, dimethylsilyl(cyclopentadienyl)(3,5-di-tert-butyl- 2-phenoxy)titanium dichloride, dimethylsilyl(cyclopentadienyl)(5-methyl-3-phenyl-2-phenoxy)titanium dichloride, dimethylsilyl(cyclopentadienyl)(3-tert-butyldimethylsilyl-5-methyl-2-phenoxy)titanium dichloride, dimethylsilyl(cyclopentadienyl)(5-methyl-3-trimethylsilyl-2-phenoxy)titanium dichloride, dimethylsilyl(cyclopentadienyl)(3-tert-butyl-5-methoxy-2-phenoxy)titanium dichloride, dimethylsilyl(cyclopentadienyl)(3-tert-butyl-5-chloro-2-phenoxy)titanium dichloride, dimethylsilyl(cyclopentadienyl)(3,5-diamyl-2-phenoxy)titanium dichloride, dimethylsilyl(methylcyclopentadienyl)(2-phenoxy)titanium dichloride, dimethylsilyl(methylcyclopentadienyl)(3-methyl-2-phenoxy)titanium dichloride, dimethylsilyl(methylcyclopentadienyl)(3,5-dimethyl-2-phenoxy)titanium dichloride, dimethylsilyl(methylcyclopentadienyl)(3-tert-butyl-2-phenoxy)titanium dichloride, dimethylsilyl(methylcyclopentadienyl)(3-tert-butyl-5-methyl-2-phenoxy)titanium dichloride, dimethylsilyl(methylcyclopentadienyl)(3,5-di-tert-butyl-2-phenoxy)titanium dichloride, dimethylsilyl(methylcyclopentadienyl)(5-methyl-3-phenyl-2-phenoxy)titanium dichloride, dimethylsilyl(methylcyclopentadienyl)(3-tert-butyldimethylsilyl-5-methyl-2-phenoxy)titanium dichloride, dimethylsilyl(methylcyclopentadienyl)(5-methyl-3-trimethylsilyl-2-phenoxy)titanium dichloride, dimethylsilyl(methylcyclopentadienyl)(3-tert-butyl-5-methoxy-2-phenoxy)titanium dichloride, dimethylsilyl(methylcyclopentadienyl)(3-tert-butyl-5-chloro-2-phenoxy)titanium dichloride, dimethylsilyl(methylcyclopentadienyl)(3,5-diamyl-2-phenoxy)titanium dichloride, dimethylsilyl(n-butylcyclopentadienyl)(2-phenoxy)titanium dichloride, dimethylsilyl(n-butylcyclopentadienyl)(3-methyl-2-phenoxy)titanium dichloride, dimethylsilyl(n-butylcyclopentadienyl)(3,5-dimethyl-2-phenoxy)titanium dichloride, dimethylsilyl(n-butylcyclopentadienyl)(3-tert-butyl-2-phenoxy)titanium dichloride, dimethylsilyl(n-butylcyclopentadienyl)(3-tert-butyl-5-methyl-2-phenoxy)titanium dichloride, dimethylsilyl(n-butylcyclopentadienyl)(3,5-di-tert-butyl-2-phenoxy)titanium dichloride, dimethylsilyl(n-butylcyclopentadienyl)(5-methyl-3-phenyl-2-phenoxy)titanium dichloride, dimethylsilyl(n-butylcyclopentadienyl)(3-tert-butyldimethylsilyl-5-methyl-2-phenoxy)titanium dichloride, dimethylsilyl(n-butylcyclopentadienyl)(5-methyl-3-trimethylsilyl-2-phenoxy)titanium dichloride, dimethylsilyl(n-butylcyclopentadienyl)(3-tert-butyl-5-methoxy-2-phenoxy)titanium dichloride, dimethylsilyl(n-butylcyclopentadienyl)(3-tert-butyl-5-chloro-2-phenoxy)titanium dichloride, dimethylsilyl(n-butylcyclopentadienyl)(3,5-diamyl-2-phenoxy)titanium dichloride, dimethylsilyl(tert-butylcyclopentadienyl)(2-phenoxy)titanium dichloride, dimethylsilyl(tert-butylcyclopentadienyl)(3-methyl-2-phenoxy)titanium dichloride, dimethylsilyl(tert-butylcyclopentadienyl)(3,5-dimethyl-2-phenoxy)titanium dichloride, dimethylsilyl(tert-butylcyclopentadienyl)(3-tert-butyl-2-phenoxy)titanium dichloride, dimethylsilyl(tert-butylcyclopentadienyl)(3-tert-butyl-5-methyl-2-phenoxy)titanium dichloride, dimethylsilyl(tert-butylcyclopentadienyl)(3,5-di-tert-butyl-2-phenoxy)titanium dichloride, dimethylsilyl(tert-butylcyclopentadienyl)(5-methyl-3-phenyl-2-phenoxy)titanium dichloride, dimethylsilyl(tert-butylcyclopentadienyl)(3-tert-butyldimethylsilyl-5-methyl-2-phenoxy)titanium dichloride, dimethylsilyl(tert-butylcyclopentadienyl)(5-methyl-3-trimethylsilyl-2-phenoxy)titanium dichloride, dimethylsilyl(tert-butylcyclopentadienyl)(3-tert-butyl-5-methoxy-2-phenoxy)titanium dichloride, dimethylsilyl(tert-butylcyclopentadienyl)(3-tert-butyl-5-chloro-2-phenoxy)titanium dichloride, dimethylsilyl(tert-butylcyclopentadienyl)(3,5-diamyl- 2-phenoxy)titanium dichloride, dimethylsilyl(tetramethylcyclopentadienyl)(2-phenoxy)titanium dichloride, dimethylsilyl(tetramethylcyclopentadienyl)(3-methyl-2-phenoxy)titanium dichloride, dimethylsilyl(tetramethylcyclopentadienyl)(3,5-dimethyl-2-phenoxy)titanium dichloride, dimethylsilyl(tetramethylcyclopentadienyl)(3-tert-butyl-2-phenoxy)titanium dichloride, dimethylsilyl(tetramethylcyclopentadienyl)(3-tert-butyl-5-methyl-2-phenoxy)titanium dichloride, dimethylsilyl(tetramethylcyclopentadienyl)(3,5-di-tert-butyl-2-phenoxy)titanium dichloride, dimethylsilyl(tetramethylcyclopentadienyl)(5-methyl-3-phenyl-2-phenoxy)titanium dichloride, dimethylsilyl(tetramethylcyclopentadienyl)(3-tert-butyldimethylsilyl-5-methyl-2-phenoxy)titanium dichloride, dimethylsilyl(tetramethylcyclopentadienyl)(5-methyl-3-trimethylsilyl-2-phenoxy)titanium dichloride, dimethylsilyl(tetramethylcyclopentadienyl)(3-tert-butyl-5-methoxy-2-phenoxy)titanium dichloride, dimethylsilyl(tetramethylcyclopentadienyl)(3-tert-butyl-5-chloro-2-phenoxy)titanium dichloride, dimethylsilyl(tetramethylcyclopentadienyl)(3,5-diamyl-2-phenoxy)titanium dichloride, dimethylsilyl(trimethylsilylcyclopentadienyl)( 2-phenoxy)titanium dichloride, dimethylsilyl(trimethylsilylcyclopentadienyl)(3-methyl-2-phenoxy)titanium dichloride, dimethylsilyl(trimethylsilylcyclopentadienyl)(3,5-dimethyl-2-phenoxy)titanium dichloride, dimethylsilyl(trimethylsilylcyclopentadienyl)(3-tert-butyl-2-phenoxy)titanium dichloride, dimethylsilyl(trimethylsilylcyclopentadienyl)(3-tert-butyl-5-methyl-2-phenoxy)titanium dichloride, dimethylsilyl(trimethylsilylcyclopentadienyl)(3,5-di-tert-butyl-2-phenoxy)titanium dichloride, dimethylsilyl(trimethylsilylcyclopentadienyl)(5-methyl-3-phenyl-2-phenoxy)titanium dichloride, dimethylsilyl(trimethylsilylcyclopentadienyl)(3-tert-butyldimethylsilyl-5-methyl-2-phenoxy)titanium dichloride, dimethylsilyl(trimethylsilylcyclopentadienyl)(5-methyl-3-trimethylsilyl-2-phenoxy)titanium dichloride, dimethylsilyl(trimethylsilylcyclopentadienyl)(3-tert-butyl-5-methoxy-2-phenoxy)titanium dichloride, dimethylsilyl(trimethylsilylcyclopentadienyl)(3-tert-butyl-5-chloro-2-phenoxy)titanium dichloride, dimethylsilyl(trimethylsilylcyclopentadienyl)(3,5-diamyl-2-phenoxy)titanium dichloride, dimethylsilyl(indenyl)(2-phenoxy)titanium dichloride, dimethylsilyl(indenyl)(3-methyl-2-phenoxy)titanium dichloride, dimethylsilyl(indenyl)(3,5-dimethyl- 2-phenoxy)titanium dichloride, dimethylsilyl(indenyl)(3-tert-butyl-2-phenoxy)titanium dichloride, dimethylsilyl(indenyl)(3-tert-butyl-5-methyl-2-phenoxy)titanium dichloride, dimethylsilyl(indenyl)(3,5-di-tert-butyl-2-phenoxy)titanium dichloride, dimethylsilyl(indenyl)(5-methyl-3-phenyl-2-phenoxy)titanium dichloride, dimethylsilyl(indenyl)(3-tert-butyldimethylsilyl-5-methyl-2-phenoxy)titanium dichloride, dimethylsilyl(indenyl)(5-methyl-3-trimethylsilyl-2-phenoxy)titanium dichloride, dimethylsilyl(indenyl)(3-tert-butyl-5-methoxy-2-phenoxy)titanium dichloride, dimethylsilyl(indenyl)(3-tert-butyl-5-chloro-2-phenoxy)titanium dichloride, dimethylsilyl(indenyl)(3,5-diamyl-2-phenoxy)titanium dichloride, dimethylsilyl(fluorenyl)(2-phenoxy)titanium dichloride, dimethylsilyl(fluorenyl)(3-methyl-2-phenoxy)titanium dichloride, dimethylsilyl(fluorenyl)(3,5-dimethyl-2-phenoxy)titanium dichloride, dimethylsilyl(fluorenyl)(3-tert-butyl-2-phenoxy)titanium dichloride, dimethylsilyl(fluorenyl)(3-tert-butyl-5-methyl-2-phenoxy)titanium dichloride, dimethylsilyl(fluorenyl)(3,5-di-tert-butyl-2-phenoxy)titanium dichloride, dimethylsilyl(fluorenyl)(5-methyl-3-phenyl- 2-phenoxy)titanium dichloride, dimethylsilyl(fluorenyl)(3-tert-butyldimethylsilyl-5-methyl-2-phenoxy)titanium dichloride, dimethylsilyl(fluorenyl)(5-methyl-3-trimethylsilyl-2-phenoxy)titanium dichloride, dimethylsilyl(fluorenyl)(3-tert-butyl-5-methoxy-2-phenoxy)titanium dichloride, dimethylsilyl(fluorenyl)(3-tert-butyl-5-chloro-2-phenoxy)titanium dichloride, dimethylsilyl(fluorenyl)(3,5-diamyl-2-phenoxy)titanium dichloride, dimethylsilyl(tetramethylcyclopentadienyl)(1-naphthox-2-yl)titanium dichloride, compounds wherein (cyclopentadienyl) of these compounds is replaced by (dimethylcyclopentadienyl), (trimethylcyclopentadienyl), (ethylcyclopentadienyl), (n-propylcyclopentadienyl), (isopropylcyclopentadienyl), (sec-butylcyclopentadienyl), (isobutylcyclopentadienyl), (tert-butyldimethylsilylcyclopentadienyl), (phenylcyclopentadienyl), (methylindenyl) or (phenylindenyl), compounds wherein (2-phenoxy) of these compounds is replaced by (3-phenyl-2-phenoxy), (3-trimethylsilyl-2-phenoxy) or (3-tert-butyldimethylsilyl-2-phenoxy), compounds wherein dimethylsilyl of these compounds is replaced by diethylsilyl, diphenylsilyl or dimethoxysilyl, compounds wherein titanium of these compounds is replaced by zirconium or hafnium, and compound wherein dichloride of these compounds is replaced by dibromide, diiodide, bis(dimethylamide), bis(diethylamide), di-n-butoxide or diisopropoxide.

The transition metal complex represented by the above general formula [I] can be synthesized, for example, by the following method.

That is, a compound having a structure that a group having a cyclopentadienyl skeleton and a group having an alkoxybenzene skeleton are combined via an atom of Group XIV is obtained by reacting an alkoxybenzene compound whose ortho-position is halogenated with a cyclopentadiene compound substituted with a halogenated atom of Group XIV in the presence of an organoalkalinemetal or a metallic magnesium. Then, a transition metal complex represented by the above general formula [I] can be synthesized by treating the compound with a base, and reacting with a transition metal halide, a transition metal hydrocarbon compound or transition metal hydrocarbonoxy compound.

(B) Aluminum Compound

The aluminum compound (B) used in the present invention includes publicly known organoaluminum compounds, that is, one or more aluminum compounds selected from (B1) an organoaluminum compound represented by the general formula $E^1_a AlZ_{3-a}$, (B2) a cyclic aluminoxane having a structure represented by the general formula $\{-Al(E^2)-O-\}_b$ and (B3) a linear aluminoxane having a structure represented by the general formula $E^3\{-Al(E^3)-O-\}_c AlE^3_2$ (wherein $E^1$, $E^2$ and $E^3$ respectively represents a hydrocarbon group, all of $E^1$, $E^2$ and $E^3$ may be the same or different; Z represents a hydrogen atom or a halogen atom, and all of Z may be the same or different; a represents a numeral satisfying $0<a\leq3$; b represents an integer of not less than 2; and c represents an integer of not less than 1). As the hydrocarbon group in $E^1$, $E^2$ or $E^3$, a hydrocarbon group having 1 to 8 carbon atoms is preferred and an alkyl group is more preferred.

Specific examples of the organoaluminum compound (B1) represented by $E^1_a AlZ_{3-a}$ include trialkylaluminums such as trimethylaluminum, triethylaluminum, tripropylaluminum, triisobutylaluminum, trihexylaluminum, etc.; dialkylaluminum chlorides such as dimethylaluminum chloride, diethylaluminum chloride, dipropylaluminum chloride, diisobutylaluminum chloride, dihexylaluminum chloride, etc.; alkylaluminum dichlorides such as methylaluminum dichloride, ethylaluminum dichloride, propylaluminum dichloride, isobutylaluminum dichloride, hexylaluminum dichloride, etc.; and dialkylaluminum hydrides such as dimethylaluminum hydride, diethylaluminum hydride, dipropylaluminum hydride, diisobutylaluminum hydride, dihexylaluminum hydride, etc.

Among them, trialkylaluminum is preferred and triethylaluminum or triisobutylaluminum is more preferred.

Specific examples of $E^2$ and $E^3$ in (B2) a cyclic aluminoxane having a structure represented by the general formula $\{-Al(E^2)-O-\}_b$ and (B3) a linear aluminoxane having a structure represented by the general formula $E^3-\{Al(E^3)-O-\}_c AlE^3_2$ include alkyl group such as methyl group, ethyl group, n-propyl group, isopropyl group, n-butyl group, isobutyl group, n-pentyl group, neopentyl group, etc. b is an integer of not less than 2, c is an integer of not less than 1. Each of $E^2$ and $E^3$ is preferably methyl group or isobutyl group. b is from 2 to 40 and c is from 1 to 40.

The above aluminoxane is prepared by various methods. The method is not specifically limited, and the aluminoxane may be prepared according to a publicly known method. For example, the aluminoxane is prepared by contacting a solution obtained by dissolving a trialkylaluminum (e.g. trimethylaluminum) in a suitable organic solvent (e.g. benzene, aliphatic hydrocarbon) with water. Also, there can be illustrated a method for preparing the aluminoxane by contacting a trialkylaluminum (e.g. trimethylaluminum, etc.) with a metal salt containing crystal water (e.g. copper sulfate hydrate, etc.).

(C) Boron Compound

As the boron compound (C) in the present invention, there can be used any one of (C1) a boron compound represented by the general formula $BQ^1Q^2Q^3$, (C2) a boron compound represented by the general formula $G^+(BQ^1Q^2Q^3Q^4)^-$ and (C3) a boron compound represented by the general formula $(L-H)^+(BQ^1Q^2Q^3Q^4)^-$.

In the boron compound (C1) represented by the general formula $BQ^1Q^2Q^3$, B represents a boron atom in the trivalent valence state; $Q^1$ to $Q^3$ may be the same or different and represent a halogen atom, a hydrocarbon group, a halogenated hydrocarbon group, a substituted silyl group, an alkoxy group or a di-substituted amino group. Each of $Q^1$ to $Q^3$ is preferably a halogen atom, a hydrocarbon group having 1 to 20 carbon atoms, a halogenated hydrocarbon group having 1 to 20 carbon atoms, a substituted silyl group having 1 to 20 carbon atoms, an alkoxy group having 1 to 20 carbon atoms or an amino group having 2 to 20 carbon atoms, more preferably a hydrocarbon group having 1 to 20 carbon atoms or a halogenated hydrocarbon group having 1 to 20 carbon atoms.

Specific examples of the compound (C1) include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, etc., most preferably tris(pentafluorophenyl)borane.

In the boron compound (C2) represented by the general formula $G^+(Q^1Q^2Q^3Q^4)^-$, $G^+$ represents an inorganic or organic cation; B represents a boron atom in the trivalent valence state; and $Q^1$ to $Q^4$ are as defined in $Q^1$ to $Q^3$.

Specific examples of $G^+$ as an inorganic cation in the compound represented by the general formula $G^+(BQ^1Q^2Q^3Q^4)^-$ include ferrocenium cation, alkyl-substituted ferrocenium cation, silver cation, etc. Examples of the $G^+$ as an organic cation include triphenylmethyl cation. $G^+$ is preferably a carbenium cation, particularly a triphenylmethyl cation.

Examples of $(BQ^1Q^2Q^3Q^4)^-$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,3,4-trifluorophenyl)borate, phenyltris(pentafluorophenyl)borate, tetrakis(3,5-bistrifluoromethylphenyl)borate, etc.

Specific combination of them include ferroceniumtetrakis(pentafluorophenyl)borate, 1,1'-dimethylferroceniumtetrakis(pentafluorophenyl)borate, silvertetrakis(pentafluorophenyl)borate, triphenylmethyltetrakis(pentafluorophenyl)borate, triphenylmethyltetrakis(3,5-bistrifluoromethylphenyl) borate, etc., most preferably triphenylmethyltetrakis (pentafluorophenyl)borate.

In the boron compound (C3) represented by the formula $(L—H)^+(BQ^1Q^2Q^3Q^4)^-$, L represents a neutral Lewis base; $(L—H)^+$ represents a Brønsted acid; B represents a boron atom in the trivalent valence state; and $Q^1$ to $Q^4$ are as defined in $Q^1$ to $Q^3$.

Specific examples of $(L—H)^+$ as a Brønsted acid in the compound represented by the formula $(L—H)^+(BQ^1Q^2Q^3Q^4)^-$ include trialkyl-substituted ammoniums, N,N-dialkyliniliniums, dialkylammoniums, triarylphosphoniums, etc., and examples of $(BQ^1Q^2Q^3Q^4)^-$ include those as defined above.

Specific combination of them include triethylammoniumtetrakis(pentafluorophenyl)borate, tripropylammoniumtetrakis(pentafluorophenyl)borate, tri(n-butyl)ammoniumtetrakis(pentafluorophenyl)borate, tri(n-butyl)ammoniumtetrakis(3,5-bistrifluoromethylphenyl) borate, N,N-dimethylaniliniumtetrakis(pentafluorophenyl) borate, N,N-diethylaniliniumtetrakis(pentafluorophenyl) borate, N,N-2,4,6-pentamethylaniliniumtetrakis (pentafluorophenyl)borate, N,N-dimethylaniliniumtetrakis (3,5-bistrifluoromethylphenyl)borate, diisopropylammoniutetrakis (pentafluorophenyl)borate, dicyclohexylammoniumtetrakis (pentafluorophenyl)borate, triphenylphosphoniumtetrakis (pentafluorophenyl)borate, tri (methylphenyl)phosphoniumtetrakis(pentafluorophenyl) borate, tri(dimethylphenyl)phosphoniumtetrakis (pentafluorophenyl)borate, etc., most preferably tri(n-butyl) ammoniumtetrakis(pentafluorophenyl)borate or N,N-dimethylanilinumtetrakis(pentafluorophenyl)borate.

[Polymerization of Olefin]

In the present invention, a catalyst for olefin polymerization, comprising a compound (A), a compound (B) and/or a compound (C) is used. In case of using a catalyst for olefin polymerization, comprising two components (A) and (B), the above cyclic aluminoxane (B2) and/or linear aluminoxane (B3) are preferable as (B). Other preferable embodiment of the catalyst for olefin polymerization includes a catalyst for olefin polymerization, comprising the above (A), (B) and (C). As (B), the above (B1) is easily used.

The respective components are desirably used so that a molar ratio of (B)/(A) is usually within the range from 0.1 to 10000, preferably 5 to 2000 and a molar ratio of (C)/(A) is usually within the range from 0.01 to 100, preferably 0.5 to 10.

When the respective components are used in the state of a solution or state suspended in a solvent, the concentration of the respective components is appropriately selected according to the conditions such as ability of an apparatus for feeding the respective components in a polymerization reactor. The respective components are desirably used so that the concentration of (A) is usually from 0.01 to 500 $\mu$mol/g, preferably from 0.05 to 100 $\mu$mol/g, more preferably from 0.05 to 50 $\mu$mol/g; the concentration of (B) is usually from 0.01 to 10000 $\mu$mol/g, preferably from 0.1 to 5000 $\mu$mol/g, more preferably from 0.1 to 2000 $\mu$mol/g, in terms of Al atom; and the concentration of (C) is usually from 0.01 to 500 $\mu$mol/g, preferably from 0.05 to 200 $\mu$mol/g, more preferably from 0.05 to 100 $\mu$mol/g.

As the olefin which can be applied to the polymerization in the present invention, olefins having 2 to 20 carbon atoms, particularly $\alpha$-olefin having 3 to 20 carbon atoms, dioelfins having 4 to 20 carbon atoms, etc. can be used. Two or more olefins can also be used, simultaneously. Specific examples of the olefin include straight-chain $\alpha$-olefins such as ethylene, propylene, butene-1, pentene-1, hexene-1, heptene-1, octene-1, nonene-1, decene-1, etc.; branched $\alpha$-olefins such as 3-methylbutene-1, 3-methylpentene-1, 4-methylpentene-1, 5-methyl-2-pentene-1, etc.; diolefins such as butadiene, isoprene, 1,4-pentadiene, 1,5-hexadiene, 1,7-octadiene, 1,9-decadiene, etc.; and styrene and vinylcyclohexane, but should not be limited to the above compounds in the present invention.

Examples of the combination of olefins in the copolymerization include ethylene and propylene, ethylene and butene-1, ethylene and pentene-1, ethylene and hexene-1, ethylene and heptene-1, ethylene and octene-1, ethylene and decene-1, propylene and butene-1, etc., but should not be limited to these combinations in the present invention.

Particularly, the content of $\alpha$-olefin of the copolymer is preferably from 4 to 60% by mol, more preferably from 5 to 55% by mol, most preferably from 6 to 50% by mol.

The present invention can be effectively applied to the preparation of the copolymer of particularly, ethylene and $\alpha$-olefin (particularly, propylene, butene-1, 4-methylpentene-1, hexene-1, octene-1, etc.) and the controllability of the density is good.

In the present invention, the polymerization is performed at a temperature of at least 130° C., preferably 135 to 350° C., under a pressure of at least 300 kg/cm$^2$, preferably 350 to 3500 kg/cm$^2$.

The polymerization may be performed in a batch-wise manner or a continuous manner, preferably a continuous manner. As a reactor, a stirring vessel type reactor or a tubular reactor can be used. The polymerization can be performed in a single reaction zone. Alternatively, the polymerization can also be performed by partitioning one reactor into a plurality of reaction zones or communicating a plurality of reactors in series or parallel. In case of using a plurality of reactors, a combination of vessel reactors or a combination of a vessel reactor and a tubular reactor. In a method for polymerizing using a plurality of reaction zones or a plurality of reactors, polymers having different characteristics can also be produced by changing the temperature, pressure and gas composition of each reaction zone.

The respective components used in the catalyst are usually fed to the reactor in the form of a solution obtained by dissolving in a suitable inert solvent or a suspension in the inert solvent, with a high-pressure pump. In the polymerization under high pressure of the present invention, the catalyst is a liquid or dissolved uniformly in an inert solvent in order to introduce the catalyst in the high-pressure portion with a pump. Alternatively, when the catalyst is a solid, which is insoluble in the solvent, those having small particle diameter and good dispersion to the solvent are preferred. In that case, the maximum particle diameter is preferably 50 $\mu$m or less. In order to control the particle diameter of the boron compound (C) or the like, there can be applied a pulverization method and a method of adding dropwise a solution obtained by dissolving in toluene to an aliphatic hydrocarbon solvent such as heptane, etc.

Examples of the suitable inert solvent include white spirit hydrocarbon oil, pentane, hexane, cyclohexane, heptane, octane, toluene, kerosine component, higher branched saturated aliphatic hydrocarbon, oligomer (e.g. isobutene oligomer, 1-butene oligomer, etc.) and mixtures thereof. A catalyst liquor is usually handled in an inert gas atmosphere such as nitrogen, argon, etc. so that is not brought into contact with water and air.

In the present invention, the above (A), (B) and (C), (A) and (B), or (A) and (C) may be introduced in the reactor after previously mixing them. Alternatively, there can be a method which comprises independently introducing them through a respective separate introducing tube and mixing them in the reactor. In case of a system of a plurality of reaction zones, they may be introduced in the first reaction zone in a single portion, or may also be introduced in other reaction zone in several portions.

The polymerization time is appropriately decided according to the kind of the desired polymer and reaction apparatus, and the conditions are not specifically limited. In the present invention, a chain transfer agent (e.g. hydrogen) can also be added to control the molecular weight of the copolymer in the present invention.

The olefin polymer of the present invention can be applied to a film, a sheet, a hollow container and an injection-molded article because of excellent transparency and strength characteristics.

The olefin polymer is particularly suitable as films and sheets, for example, various packaging films or sheets, agricultural films or sheets and films or sheets for laminating, or the like which are formed by inflation film forming, T-die forming, calender forming, etc.

Furthermore, the olefin polymer of the present invention can also be suitable as usage such as inner thin-wall container (e.g. container for mayonnaise/ketchup, tubular container for cosmetic/size, container for seasoning, corrugated box/metal container, etc.), blow molded article (e.g. container for detergent, cosmetic, drug, etc.), injection molded article (e.g. lid of container, cap and inside plug of bottle, cap or cover of part, artificial grass, sky shoes, automobile mad guard, etc.), foamed molded article (e.g. tray for stretch packaging, foamed box, container for instant food, etc.), various molded articles (e.g. pipe for waterwork/agriculture, other sundries, industrial parts, etc.), or coating material (e.g. coating of electric wire/cable, sheath or wiring of power/communication cable, steel pipe coating such as extrusion coating onto a steel pipe using cross head die, etc.), in addition to film and sheet.

Furthermore, the olefin polymer of the present invention can be molded into a multi-layer film or sheet of two or more layers of the other material by using various publicly known methods such as co-extrusion method, dry lamination method, sandwich lamination method, extrusion lamination method, etc. As the other material, for example, there can be used publicly known materials such as paper, board, aluminum thin film, cellophane, nylon, PET, PP, polyvinylidene chloride, EVOH, various adhesive resins, etc.

The olefin polymer of the present invention can contain publicly known additives such as antioxidants, weathering agents, lubricants, anti-blocking agents, antistatic agents, anti-fogging agents, anti-dropping agents, pigments, fillers, etc., if necessary. The olefin polymer of the present invention further may be blended with a publicly known polymer substance such as radical polymerization method low-density polyethylene, high-density polyethylene, linear low-density polyethylene, ethylene-α-olefin copolymer elastomer, polypropylene, poly 1-butene, poly 4-methyl-1-pentene or the like.

The transparency and strength characteristics in the present invention are evaluated by using molded products such as film, sheet, hollow container, injection-molded article, etc. Evaluation can also be performed by using a pressed sheet as a simple evaluation method.

BRIEF DESCRIPTION OF THE DRAWINGS

FIG. 2 is a flow chart for assisting the understanding of the present invention. This flow chart is a typical example of an embodiment of the present invention, and the present invention is not limited thereto.

BEST MODE FOR CARRYING OUT THE INVENTION

Figure 1:
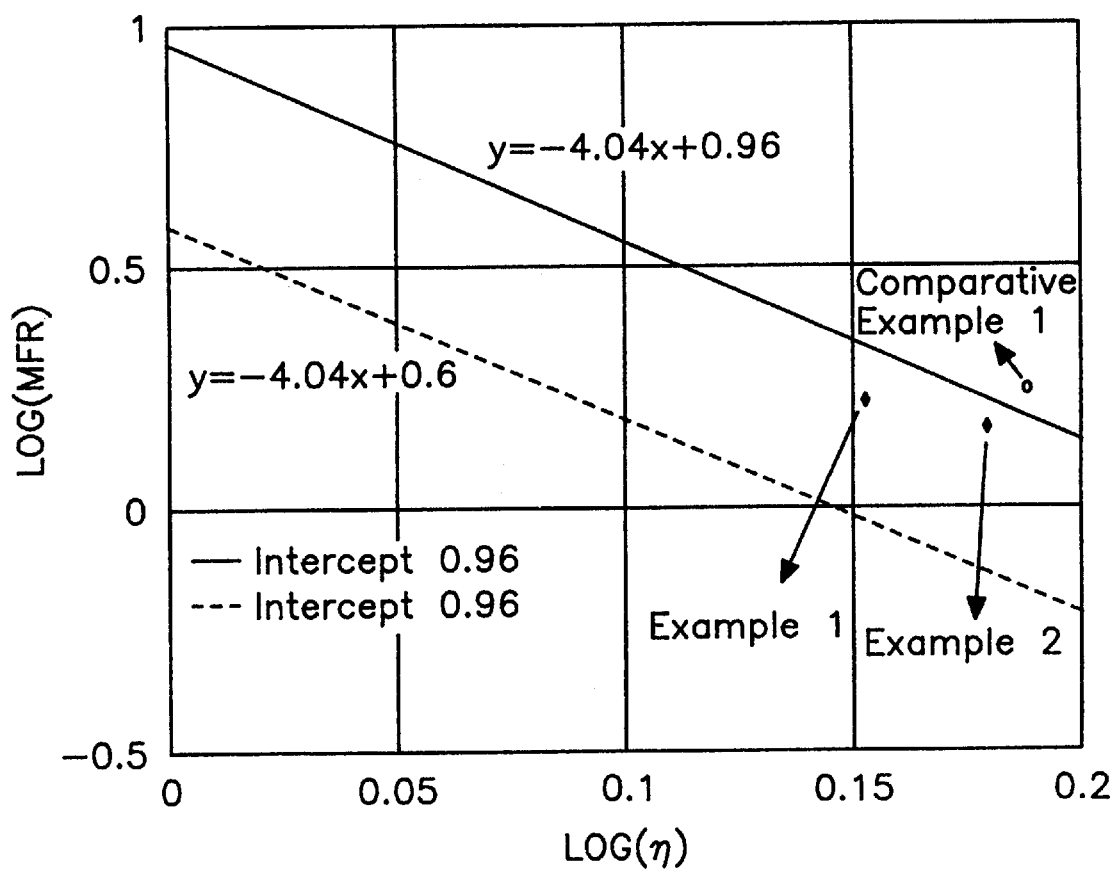
FIG. 1 shows a relation between the melt flow rate (MFR) and the intrinsic viscosity [η] measured in tetralin at 135° C. in the olefin copolymers used in the Examples and Comparative Example.

The following Examples and Comparative Examples further illustrate the present invention in detail but are not to be construed to limit the scope thereof. Properties of the polymers in the Examples were measured by the following methods.

(1) Melt flow rate (MFR): It was measured at 190° C. under a load of 2.16 kg according to the method defined in JIS K-6760.

(2) Intrinsic viscosity [η]: It was measured in tetralin at 135° C. by using an Ubbelohde viscometer.

(3) The density was determined according to JIS K-6760. Provided that the value of the density described as the density (without annealing) is a value measured without subjecting to annealing, whereas the value of the density described as the density (after annealing) is a value measured after annealing.

(4) Melting point of copolymer: It was measured under the following conditions by using DSC7 manufactured by Perkin-Elmer Co.

Heating: heating to 150° C. and maintaining at the same temperature until calorie is stabilized Cooling: cooling from 150 to 40° C. (5° C./min.) and maintaining for 2 minutes Measurement: measured at the temperature within the range from 10 to 150° C. (5° C./min.)

(5) Content of α-olefin: It was determined from characteristic absorption of ethylene and a-olefin by using an infrared spectrometer (FT-IR7300, manufactured by NIPPON BUNKO Inc.) and was shown as the short-chain branch (SCB) number per 1000 carbon atoms.

(6) Molecular weight and molecular weight distribution: They were determined under the following conditions by using gel permeation chromatograph (150, C, manufactured by Waters Co.).

Column: TSK gel GMH-HT

Measuring temperature: set at 145° C.

Measuring concentration: 10 mg/10 ml orthodichlorobenzene (7) Film Forming

A die (lip distance: 2 mm) was mounted to a EX-50 type inflation molding machine (manufactured by Plako Co.) at a diameter of 125 mm φ and an inflation film molding was performed under the conditions of a molding temperature of 160° C., a blow-up ratio of 1.8 and an extrusion amount of 25 kg/hour to prepare a film having a thickness of 30 μm and a film having a thickness of 80 μm, respectively.

(8) Haze of Film

It was measured by using the method defined in ASTM D1003.

(9) Tear Strength

It was measured by using the method defined in JIS P-8116.

REFERENCE EXAMPLE (Synthesis of Transition Metal Complex: dimethylsilyl(tetramethylcyclopentadienyl)(3-tert-butyl-5-methyl-2-phenoxy)titanium Dichloride (1) Synthesis of 1-bromo-3-tert-butyl-5-methyl-2-phenol Under a nitrogen atmosphere, 20.1 g (123 mmol) of 2-tert-butyl-4-methylphenol was dissolved in 150 ml of toluene in a 500 ml four-necked flask equipped with a stirrer, and 25.9 ml (18.0 g, 246 mmol) of tert-butylamine was then added. This solution was cooled to −70° C. and 10.5 ml (32.6 g, 204 mmol) of bromine was added to the solution. The mixture was stirred for 2 hours at −70° C. Thereafter, the mixture was heated to room temperature and washed three times by adding 100 ml of 10% diluted hydrochloric acid every washing. After washing, the resulting organic layer was dried by using anhydrous sodium sulfate and the solvent was removed by using an evaporator. Then, the organic layer was purified by using a silica gel column to obtain 18.4 g (75.7 mmol) of 1-bromo-3-tert-butyl-5-methyl-2-phenol as a colorless oil. The yield was 62%.

(2) Synthesis of 1-bromo-3-tert-butyl-2-methoxy-5-methylbenzene

Under a nitrogen atmosphere, 13.9 g (57.2 mmol) of 1-bromo-3-tert-butyl-5-methyl-2-phenol synthesized in the above (1) was dissolved in 40 ml of acetonitrile in a 100 ml four-necked flask equipped with a stirrer, and 3.8 g (67.9 mmol) of potassium hydroxide was then added. Furthermore, 17.8 ml (40.6 g, 286 mmol) of methyl iodide was added, followed by continuous stirring for 12 hours. Then, the solvent was removed by using an evaporator and 40 ml of hexane was added to the residue, thereby to extract the hexane soluble matter. The extraction was repeated three times. The solvent was removed from the extract to obtain 13.8 g (53.7 mmol) of 1-bromo-3-tert-butyl-2-methoxy-5-methylbenzene as a pale yellow oil. The yield was 94%.

(3) Synthesis of (3-tert-butyl-2-methoxy-5-methylphenyl) chlorodimethylsilane

To a solution of tetrahydrofuran (31.5 ml), hexane (139 ml) and 1-bromo-3-tert-butyl-2-methoxy-5-methylbenzene (45 g) synthesized in the above (2), a hexane solution (115 ml) of n-butyllithium (1.6 mol/liter) was added dropwise at −40° C. over 20 minutes. After the resulting mixture was maintained at −40° C. for 1 hour, tetrahydrofuran (31.5 ml) was added dropwise.

To a solution of dichlorodimethylsilane (131 g) and hexane (306 ml), the mixture obtained above was added dropwise at −40° C. The resulting mixture was heated to room temperature over 2 hours, followed by stirring at room temperature for 12 hours.

The solvent and excess dichlorodimethylsilane were distilled off from the reaction mixture under reduced pressure, and the hexane soluble matter was extracted with hexane from the residue. Then, the solvent was distilled off from the resulting hexane solution to obtain 41.9 g of (3-tert-butyl-2-methoxy-5-methylphenyl) chlorodimethylsilane as a pale yellow oil. The yield was 84%.

(4) Synthesis of (3-tert-butyl-2-methoxy-5-ethylphenyl) dimethyl(tetramethylcyclopentadienyl)silane To a solution of (3-tert-butyl-2-methoxy-5-methylphenyl) chlorodimethylsilane (5.24 g) synthesized in the above (3) and tetrahydrofuran (50 ml), tetramethylcyclopentadienyl lithium (2.73 g) was added at −35° C. and the mixture was heated to room temperature over 2 hours, followed by stirring at room temperature for 10 hours.

The solvent was distilled off from the resulting reaction mixture under reduced pressure, and the hexane soluble matter was extracted with hexane from the residue. Then, the solvent was distilled off from the resulting hexane solution under reduced pressure to obtain 6.69 g of (3-tert-butyl-2-methoxy-5-methylphenyl)dimethyl (tetramethylcyclopentadienyl)silane as an yellow oil. The yield was 97%.

(5) Synthesis of Dimethylsilyl(tetramethylcyclopentadienyl)(3-tert-butyl-5-methyl-2-phenoxy)titanium Dichloride To a solution of (3-tert-butyl-2-methoxy-5-methylphenyl) dimethyl(tetramethylcyclopentadienyl)silane (10.04 g) synthesized in the above (4), toluene (100 ml) and triethylamine (6.30 g), a hexane solution (19.0 ml) of n-butyllithium (1.63 mol/liter) was added dropwise at −70° C. Then, the mixture was heated to room temperature over 2 hours and maintained at room temperature for 12 hours.

Under a nitrogen atmosphere, the mixture obtained above was added dropwise to a toluene solution (50 ml) of titanium tetrachloride (4.82 g) at 0° C. The resulting mixture was heated to room temperature over 1 hour and heated under reflux for 10 hours.

The reaction mixture was filtered and the solvent was distilled off from the filtrate. The residue was recrystallized from a toluene-hexane mixed solvent to obtain 3.46 g of dimethylsilyl(tetramethylcyclopentadienyl)(3-tert-butyl-5-methyl-2-phenoxy)titanium dichloride as an orange prismatic crystal. The yield was 27%.

The spectrum data were as follows.

$^1$H-NMR (CDCl$_3$) δ 0.57 (s, 6H), 1.41 (s, 9H), 2.15 (s, 6H), 2.34 (s, 6H), 2.38 (s, 3H), 7.15 (s, 1H), 7.18 (s, 1H)

$^{13}$C-NMR (CDCl$_3$) δ 1.25, 14.48, 16.28, 22.47, 31.25, 36.29, 120.23, 130.62, 131.47, 133.86, 135.50, 137.37, 140.82, 142.28, 167.74

Mass spectrum (CI, m/e)458

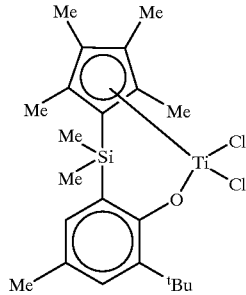

Example 1

Using an autoclave type reactor having an internal volume of 1 liter, equipped with a stirring blade, ethylene and hexene-1 were continuously fed in a reactor and polymerization was performed. Regarding the polymerization conditions, the total pressure was set to 800 kg/cm$^2$G and the concentration of hexene-1 was set to 34% by mol. A hexane solution (0.7 μmol/g) of dimethylsilyl (tetramethylcyclopentadienyl)(3-tert-butyl-5-methyl-2-phenoxy)titanium dichloride, a heptane solution (33 μmol/g) of triisobutylaluminum and a toluene solution (1.2 μmol/g) of N,N-dimethylaniliniumtetrakis(pentafluorophenyl)borate were prepared in separate vessels, and the respective solutions were continuously fed in the reactor at a feeding rate of 290 g/hour, 350 g/hour and 580 g/hour, respectively. The polymerization reaction temperature was set to 215° C., a molar ratio of Al atom to Ti atom was set to 57, and a molar ratio of boron atom to Ti atom was set to 3.3. As a result, an ethylene-hexene-1 copolymer having MFR of 4.2, a density (without annealing) of 0.881, a melting point of 67.3° C., SCB of 40.4, a molecular weight (Mw) of 66000 and a molecular weight distribution (Mw/Mn) of 1.8 was produced in a rate of 14 ton per one hour per mol of Ti atom.

Example 2

Using an autoclave type reactor having an internal volume of 1 liter, equipped with a stirring blade, ethylene and hexene-1 were continuously fed in a reactor and polymerization was performed. Regarding the polymerization conditions, the total pressure was set to 800 kg/cm$^2$G and the concentration of hexene-1 was set to 30% by mol. A hexane solution (0.7 g mol/g) of dimethylsilyl (tetramethylcyclopentadienyl)(3-tert-butyl-5-methyl-2-phenoxy)titanium dichloride, a heptane solution (33 μmol/g) of triisobutylaluminum and a toluene solution (1.2 μmol/g) of N,N-dimethylaniliniumtetrakis(pentafluorophenyl)borate were prepared in separate vessels, and the respective solutions were continuously fed in the reactor at a feeding rate of 290 g/hour, 355 g/hour and 565 g/hour, respectively. The polymerization reaction temperature was set to 223° C., a molar ratio of Al atom to Ti atom was set to 57, and a molar ratio of boron atom to Ti atom was set to 3.2. As a result, an ethylene-hexene-1 copolymer having MFR of 3.3, a density (without annealing) of 0.887, a melting point of 73.5° C., SCB of 36.6, a molecular weight (Mw) of 70000 and a molecular weight distribution (Mw/Mn) of 1.9 was produced in a rate of 15 ton per one hour per mol of Ti atom.

Example 3

Using an autoclave type reactor having an internal volume of 1 liter, equipped with a stirring blade, ethylene and hexene-1 were continuously fed in a reactor and polymerization was performed. Regarding the polymerization conditions, the total pressure was set to 800 kg/cm$^2$G and the concentration of hexene-1 was set to 27% by mol. A hexane solution (0.7 μmol/g) of dimethylsilyl (tetramethylcyclopentadienyl)(3-tert-butyl-5-methyl-2-phenoxy)titanium dichloride, a heptane solution (33 μmol/g) of triisobutylaluminum and a toluene solution (1.2 μmol/g) of N,N-dimethylaniliniumtetrakis(pentafluorophenyl)borate were prepared in separate vessels, and the respective solutions were continuously fed in the reactor at a feeding rate of 240 g/hour, 290 g/hour and 550 g/hour, respectively. The polymerization reaction temperature was set to 230° C., a molar ratio of Al atom to Ti atom was set to 55, and a molar ratio of boron atom to Ti atom was set to 3.6. As a result, an ethylene-hexene-1 copolymer having MFR of 2.5, a density (without annealing) of 0.892, a melting point of 80.6° C., SCB of 29.8, a molecular weight (Mw) of 76000 and a molecular weight distribution (Mw/Mn) of 1.8 was produced in a rate of 17 ton per one hour per mol of Ti atom.

Example 4

Using an autoclave type reactor having an internal volume of 1 liter, equipped with a stirring blade, ethylene and hexene-1 were continuously fed in a reactor and polymerization was performed. Regarding the polymerization conditions, the total pressure was set to 900 kg/cm$^2$G, the concentration of hexene-1 was set to 23% by mol and the concentration of hydrogen was set to 0.05% by mol. A hexane solution (0.7 μmol/g) of dimethylsilyl (tetramethylcyclopentadienyl)(3-tert-butyl-5-methyl-2-phenoxy)titanium dichloride, a heptane solution (33 μmol/g) of triisobutylaluminum and a toluene solution (1.2 μmol/g) of N,N-dimethylaniliniumtetrakis(pentafluorophenyl)borate were prepared in separate vessels, and the respective solutions were continuously fed in the reactor at a feeding rate of 210 g/hour, 270 g/hour and 488 g/hour, respectively. The polymerization reaction temperature was set to 231° C., a molar ratio of Al atom to Ti atom was set to 64, and a molar ratio of boron atom to Ti atom was set to 3.9. As a result, an ethylene-hexene-1 copolymer having MFR of 1.7, a density (without annealing) of 0.897, a density (after annealing) of 0.901, a melting point of 94.6° C., SCB of 25.0, a molecular weight (Mw) of 79000 and a molecular weight distribution (Mw/Mn) of 1.8 was produced in a rate of 18 ton per one hour per mol of Ti atom.

Example 5

Using an autoclave type reactor having an internal volume of 1 liter, equipped with a stirring blade, ethylene and hexene-1 were continuously fed in a reactor and polymerization was performed. Regarding the polymerization conditions, the total pressure was set to 900 kg/cm$^2$G and the concentration of hexene-1 was set to 33% by mol. A hexane solution (0.7 μmol/g) of dimethylsilyl (tetramethylcyclopentadienyl)(3-tert-butyl-5-methyl-2-phenoxy)titanium dichloride, a heptane solution (33 μmol/g) of triisobutylaluminum and a toluene solution (1.2 μmol/g) of N,N-dimethylaniliniumtetrakis(pentafluorophenyl)borate were prepared in separate vessels, and the respective solutions were continuously fed in the reactor at a feeding rate of 106 g/hour, 195 g/hour and 420 g/hour, respectively. The polymerization reaction temperature was set to 202° C., a molar ratio of Al atom to Ti atom was set to 85, and a molar ratio of boron atom to Ti atom was set to 6.7. As a result, an ethylene-hexene-1 copolymer having MFR of 2.8, a density (without annealing) of 0.880, SCB of 38.7, a molecular weight (Mw) of 77000 and a molecular weight distribution (Mw/Mn) of 1.9 was produced in a rate of 28 ton per one hour per mol of Ti atom.

Example 6

Using an autoclave type reactor having an internal volume of 1 liter, equipped with a stirring blade, ethylene and hexene-1 were continuously fed in a reactor and polymerization was performed. Regarding the polymerization conditions, the total pressure was set to 900 kg/cm$^2$G and the concentration of hexene-1 was set to 32% by mol. A hexane solution (0.7 μmol/g) of dimethylsilyl (tetramethylcyclopentadienyl)(3-tert-butyl-5-methyl-2-phenoxy)titanium dichloride, a heptane solution (33 μmol/g) of triisobutylaluminum and a toluene solution (1.2 μmol/g) of N,N-dimethylaniliniumtetrakis(pentafluorophenyl)borate were prepared in separate vessels, and the respective solutions were continuously fed in the reactor at a feeding rate of 60 g/hour, 110 g/hour and 260 g/hour, respectively. The polymerization reaction temperature was set to 195° C., a molar ratio of Al atom to Ti atom was set to 84, and a molar ratio of boron atom to Ti atom was set to 6.7. As a result, an ethylene-hexene-1 copolymer having MFR of 2.3, a density (no annealing) of 0.879, SCB of 40.4, a molecular weight (Mw) of 82000 and a molecular weight distribution (Mw/Mn) of 1.8 was produced in a rate of 43 ton per one hour per mol of Ti atom.

Example 7

Using an autoclave type reactor having an internal volume of 1 liter, equipped with a stirring blade, ethylene and hexene-1 were continuously fed in a reactor and polymerization was performed. Regarding the polymerization conditions, the total pressure was set to 900 kg/cm$^2$G, the concentration of hexene-1 was set to 14% by mol and the concentration of hydrogen was set to 0.20% by mol. A hexane solution (0.7 μmol/g) of dimethylsilyl (tetramethylcyclopentadienyl)(3-tert-butyl-5-methyl-2-phenoxy)titanium dichloride, a heptane solution (33 μmol/g) of triisobutylaluminum and a toluene solution (1.2 μmol/g) of N,N-dimethylaniliniumtetrakis(pentafluorophenyl)borate were prepared in separate vessels, and the respective solutions were continuously fed in the reactor at a feeding rate of 200 g/hour, 240 g/hour and 365 g/hour, respectively. The polymerization reaction temperature was set to 229° C., a molar ratio of Al atom to Ti atom was set to 56, and a molar ratio of boron atom to Ti atom was set to 3.0. As a result, an ethylene-hexene-1 copolymer having MFR of 1.5, a density (without annealing) of 0.908, a density (after annealing) of 0.913, a melting point of 108° C., SCB of 15.5, a molecular weight (Mw) of 81000 and a molecular weight distribution (Mw/Mn) of 1.8 was produced in a rate of 15 ton per one hour per mol of Ti atom.

Example 8

Using an autoclave type reactor having an internal volume of 1 liter, equipped with a stirring blade, ethylene and hexene-1 were continuously fed in a reactor and polymerization was performed. Regarding the polymerization conditions, the total pressure was set to 800 kg/cm$^2$G and the concentration of hexene-1 was set to 37% by mol. A hexane solution (0.2 $\mu$mol/g) of dimethylsilyl(tetramethylcyclopentadienyl)(3-tert-butyl-5-methyl-2-phenoxy)titanium dichloride, a heptane solution (10 $\mu$mol/g) of triisobutylaluminum and a toluene solution (0.9 $\mu$mol/g) of N,N-dimethylaniliniumtetrakis(pentafluorophenyl)borate were prepared in separate vessels, and the respective solutions were continuously fed in the reactor at a feeding rate of 80 g/hour, 80 g/hour and 110 g/hour, respectively. The polymerization reaction temperature was set to 190° C., a molar ratio of Al atom to Ti atom was set to 50, and a molar ratio of boron atom to Ti atom was set to 6.0. As a result, an ethylene-hexene-1 copolymer having MFR of 5.6, a density (without annealing) of 0.866, a melting point of 57.1° C., SCB of 52.0, a molecular weight (Mw) of 70000 and a molecular weight distribution (Mw/Mn) of 1.8 was produced in a rate of 110 ton per one hour per mol of Ti atom.

Example 9

Using an autoclave type reactor having an internal volume of 1 liter, equipped with a stirring blade, ethylene and hexene-1 were continuously fed in a reactor and polymerization was performed. Regarding the polymerization conditions, the total pressure was set to 800 kg/cm$^2$G and the concentration of hexene-1 was set to 34% by mol. A hexane solution (0.2 $\mu$mol/g) of dimethylsilyl(tetramethylcyclopentadienyl)(3-tert-butyl-5-methyl-2-phenoxy)titanium dichloride, a heptane solution (10 $\mu$mol/g) of triisobutylaluminum and a toluene solution (0.45 $\mu$mol/g) of N,N-dimethylaniliniumtetrakis(pentafluorophenyl)borate were prepared in separate vessels, and the respective solutions were continuously fed in the reactor at a feeding rate of 120 g/hour, 130 g/hour and 170 g/hour, respectively. The polymerization reaction temperature was set to 190° C., a molar ratio of Al atom to Ti atom was set to 55, and a molar ratio of boron atom to Ti atom was set to 3.5. As a result, an ethylene-hexene-1 copolymer having MFR of 4.2, a density (without annealing) of 0.869, a melting point of 58.0° C., SCB of 49.7, a molecular weight (Mw) of 72000 and a molecular weight distribution (Mw/Mn) of 1.8 was produced in a rate of 70 ton per one hour per mol of Ti atom.

Example 10

Using an autoclave type reactor having an internal volume of 1 liter, equipped with a stirring blade, ethylene and hexene-1 were continuously fed in a reactor and polymerization was performed. Regarding the polymerization conditions, the total pressure was set to 800 kg/cm$^2$G and the concentration of hexene-1 was set to 33% by mol. A hexane solution (0.4 $\mu$mol/g) of dimethylsilyl(tetramethylcyclopentadienyl)(3-tert-butyl-5-methyl-2-phenoxy)titanium dichloride, a heptane solution (20 $\mu$mol/g) of triisobutylaluminum and a toluene solution (0.9 $\mu$mol/g) of N,N-dimethylaniliniumtetrakis(pentafluorophenyl)borate were prepared in separate vessels, and the respective solutions were continuously fed in the reactor at a feeding rate of 680 g/hour, 740 g/hour and 1000 g/hour, respectively. The polymerization reaction temperature was set to 224° C., a molar ratio of Al atom to Ti atom was set to 55, and a molar ratio of boron atom to Ti atom was set to 3.3. As a result, an ethylene-hexene-1 copolymer having MFR of 5.8, a density (without annealing) of 0.882, a melting point of 64.3° C., SCB of 40.0, a molecular weight (Mw) of 65000 and a molecular weight distribution (Mw/Mn) of 1.8 was produced in a rate of 11 ton per one hour per mol of Ti atom.

Example 11

Using an autoclave type reactor having an internal volume of 1 liter, equipped with a stirring blade, ethylene and hexene-1 were continuously fed in a reactor and polymerization was performed. Regarding the polymerization conditions, the total pressure was set to 800 kg/cm$^2$G, the concentration of hexene-1 was set to 24% by mol and the concentration of hydrogen was set to 0.11% by mol. A hexane solution (0.4 $\mu$/mol/g) of dimethylsilyl(tetramethylcyclopentadienyl)(3-tert-butyl-5-methyl-2-phenoxy)titanium dichloride, a heptane solution (20 $\mu$mol/g) of triisobutylaluminum and a toluene solution (0.9 $\mu$mol/g) of N,N-dimethylaniliniumtetrakis(pentafluorophenyl)borate were prepared in separate vessels, and the respective solutions were continuously fed in the reactor at a feeding rate of 470 g/hour, 530 g/hour and 530 g/hour, respectively. The polymerization reaction temperature was set to 231° C., a molar ratio of Al atom to Ti atom was set to 55, and a molar ratio of boron atom to Ti atom was set to 2.6. As a result, an ethylene-hexene-1 copolymer having MFR of 7.8, a density (without annealing) of 0.897, a melting point of 92.8° C., SCB of 28.4, a molecular weight (Mw) of 58000 and a molecular weight distribution (Mw/Mn) of 1.9 was produced in a rate of 13 ton per one hour per mol of Ti atom.

Example 12

Using an autoclave type reactor having an internal volume of 1 liter, equipped with a stirring blade, ethylene and octene-1 were continuously fed in a reactor and polymerization was performed. Regarding the polymerization conditions, the total pressure was set to 800 kg/cm$^2$G and the concentration of octene-1 was set to 20% by mol. A hexane solution (0.7 $\mu$mol/g) of dimethylsilyl(tetramethylcyclopentadienyl)(3-tert-butyl-5-methyl-2-phenoxy)titanium dichloride, a heptane solution (114 a mol/g) of triisobutylaluminum and a toluene solution (0.9 $\mu$/mol/g) of N,N-dimethylaniliniumtetrakis(pentafluorophenyl)borate were prepared in separate vessels, and the respective solutions were continuously fed in the reactor at a feeding rate of 180 g/hour, 180 g/hour and 440 g/hour, respectively. The polymerization reaction temperature was set to 234° C., a molar ratio of Al atom to Ti atom was set to 150, and a molar ratio of boron atom to Ti atom was set to 3.0. As a result, an ethylene-octene-1 copolymer having MFR of 4.7, a density (without annealing) of 0.891, a melting point of 91.9° C., SCB of 26.7, a molecular weight (Mw) of 71000 and a molecular weight distribution (Mw/Mn) of 1.8 was produced in a rate of 22 ton per one hour per mol of Ti atom.

Example 13

Using an autoclave type reactor having an internal volume of 1 liter, equipped with a stirring blade, ethylene and octene-1 were continuously fed in a reactor and polymerization was performed. Regarding the polymerization conditions, the total pressure was set to 800 kg/cm$^2$G and the concentration of octene-1 was set to 33% by mol. A hexane solution (0.7 µmol/g) of dimethylsilyl(tetramethylcyclopentadienyl)(3-tert-butyl-5-methyl-2-phenoxy)titanium dichloride, a heptane solution (150 µmol/g) of triisobutylaluminum and a toluene solution (0.9 µmol/g) of N,N-dimethylaniliniumtetrakis(pentafluorophenyl)borate were prepared in separate vessels, and the respective solutions were continuously fed in the reactor at a feeding rate of 80 g/hour, 90 g/hour and 380 g/hour, respectively. The polymerization reaction temperature was set to 185° C., a molar ratio of Al atom to Ti atom was set to 280, and a molar ratio of boron atom to Ti atom was set to 8.0. As a result, an ethylene-octene-1 copolymer having MFR of 5.1, a density (without annealing) of 0.869, a melting point of 60.2° C., SCB of 39.8, a molecular weight (Mw) of 72000 and a molecular weight distribution (Mw/Mn) of 1.7 was produced in a rate of 33 ton per one hour per mol of Ti atom.

Example 14

Using an autoclave type reactor having an internal volume of 1 liter, equipped with a stirring blade, ethylene and butene-1 were continuously fed in a reactor and polymerization was performed. Regarding the polymerization conditions, the total pressure was set to 800 kg/cm$^2$G and the concentration of butene-1 was set to 46% by mol. A hexane solution (0.2 µmol/g) of dimethylsilyl(tetramethylcyclopentadienyl)(3-tert-butyl-5-methyl-2-phenoxy)titanium dichloride, a heptane solution (35 µmol/g) of triisobutylaluminum and a toluene solution (0.45 µmol/g) of N,N-dimethylaniliniumtetrakis(pentafluorophenyl)borate were prepared in separate vessels, and the respective solutions were continuously fed in the reactor at a feeding rate of 70 g/hour, 90 g/hour and 130 g/hour, respectively. The polymerization reaction temperature was set to 194° C., a molar ratio of Al atom to Ti atom was set to 200, and a molar ratio of boron atom to Ti atom was set to 4.0. As a result, an ethylene-butene-1 copolymer having MFR of 2.8, a density (without annealing) of 0.869, a melting point of 56.7° C., SCB of 58.0, a molecular weight (Mw) of 80000 and a molecular weight distribution (Mw/Mn) of 1.7 was produced in a rate of 110 ton per one hour per mol of Ti atom.

Example 15

Using an autoclave type reactor having an internal volume of 1 liter, equipped with a stirring blade, ethylene and butene-1 were continuously fed in a reactor and polymerization was performed. Regarding the polymerization conditions, the total pressure was set to 800 kg/cm$^2$G and the concentration of butene-1 was set to 46% by mol. A hexane solution (0.2 µmol/g) of dimethylsilyl(tetramethylcyclopentadienyl)(3-tert-butyl-5-methyl-2-phenoxy)titanium dichloride, a heptane solution (10 µmol/g) of triisobutylaluminum and a toluene solution (0.45 µmol/g) of N,N-dimethylaniliniumtetrakis(pentafluorophenyl)borate were prepared in separate vessels, and the respective solutions were continuously fed in the reactor at a feeding rate of 90 g/hour, 110 g/hour and 170 g/hour, respectively. The polymerization reaction temperature was set to 205° C., a molar ratio of Al atom to Ti atom was set to 60, and a molar ratio of boron atom to Ti atom was set to 4.0. As a result, an ethylene-butene-1 copolymer having MFR of 5.2, a density (without annealing) of 0.868, a melting point of 56.7° C., SCB of 61.1, a molecular weight (Mw) of 66000 and a molecular weight distribution (Mw/Mn) of 1.8 was produced in a rate of 90 ton per one hour per mol of Ti atom.

Example 16

Using an autoclave type reactor having an internal volume of 1 liter, equipped with a stirring blade, ethylene and butene-1 were continuously fed in a reactor and polymerization was performed. Regarding the polymerization conditions, the total pressure was set to 800 kg/cm$^2$G, the concentration of butene-1 was set to 29% by mol and the concentration of hydrogen was set to 0.06% by mol. A hexane solution (0.7 µmol/g) of dimethylsilyl(tetramethylcyclopentadienyl)(3-tert-butyl-5-methyl-2-phenoxy)titanium dichloride, a heptane solution (35 µmol/g) of triisobutylaluminum and a toluene solution (0.9 µmol/g) of N,N-dimethylaniliniumtetrakis(pentafluorophenyl)borate were prepared in separate vessels, and the respective solutions were continuously fed in the reactor at a feeding rate of 230 g/hour, 280 g/hour and 670 g/hour, respectively. The polymerization reaction temperature was set to 230° C., a molar ratio of Al atom to Ti atom was set to 60, and a molar ratio of boron atom to Ti atom was set to 3.5. As a result, an ethylene-butene-1 copolymer having MFR of 1.8, a density (without annealing) of 0.897, a melting point of 90.7° C., SCB of 30.4, a molecular weight (Mw) of 82000 and a molecular weight distribution (Mw/Mn) of 1.9 was produced in a rate of 10 ton per one hour per mol of Ti atom.

Example 17

Using an autoclave type reactor having an internal volume of 1 liter, equipped with a stirring blade, ethylene and butene-1 were continuously fed in a reactor and polymerization was performed. Regarding the polymerization conditions, the total pressure was set to 800 kg/cm$^2$G, the concentration of butene-1 was set to 29% by mol and the concentration of hydrogen was set to 0.13% by mol. A hexane solution (0.7 µmol/g) of dimethylsilyl(tetramethylcyclopentadienyl)(3-tert-butyl-5-methyl-2-phenoxy)titanium dichloride, a heptane solution (35 µmol/g) of triisobutylaluminum and a toluene solution (0.9 µmol/g) of N,N-dimethylaniliniumtetrakis(pentafluorophenyl)borate were prepared in separate vessels, and the respective solutions were continuously fed in the reactor at a feeding rate of 300 g/hour, 380 g/hour and 700 g/hour, respectively. The polymerization reaction temperature was set to 230° C., a molar ratio of Al atom to Ti atom was set to 60, and a molar ratio of boron atom to Ti atom was set to 3.0. As a result, an ethylene-butene-1 copolymer having MFR of 4.6, a density (without annealing) of 0.899, a melting point of 92.5° C., SCB of 30.0, a molecular weight (Mw) of 65000 and a molecular weight distribution (Mw/Mn) of 1.8 was produced in a rate of 10 ton per one hour per mol of Ti atom.

Example 18

Using an autoclave type reactor having an internal volume of 1 liter, equipped with a stirring blade, ethylene and butene-1 were continuously fed in the reactor and polymerization was carried out. The polymerization conditions were set to the total pressure of 800 kg/cm$^2$G, the concentration of butene-1 of 29% by mol and the concentration of hydrogen of 0.12% by mol. A hexane solution (0.7 µmol/g) of dimethylsilyl (tetramethylcyclopentadienyl)(3-tert-butyl-5-methyl-2-phenoxy)titanium dichloride, a heptane solution (35 µmol/g) of triisobutylaluminum and N,N-dimethylaniliniumtetrakis(pentafluorophenyl)borate (obtained by atomizing according to a re-precipitation method using toluene and heptane, the particle size is from 2 to 3 µm and particles having the particle size of not less than 10 µm are not observed, 1.2 µmol/g) dispersed in a mixed solution (a volume ratio of heptane: liquid paraffin= 1:4) of heptane and liquid paraffin (Crystol 202, manufactured by Esso Sekiyu K.K.) were prepared in separate vessels, and the respective ones were continuously fed in the reactor at a feeding rate of 300 g/hour, 360 g/hour and 750 g/hour, respectively. The polymerization temperature was set to 230° C., a molar ratio of Al atom to Ti atom was set to 60, and a molar ratio of boron atom to Ti atom was set to 4.4. As a result, an ethylene-butene-1 copolymer having a melting point of 90.6° C., a molecular weight (Mw) of 64000 and a molecular weight distribution (Mw/Mn) of 1.7 was produced in a rate of 10 ton per one hour per mol of Ti atom.

Example 19

Using an autoclave type reactor having an internal volume of 1 liter, equipped with a stirring blade, ethylene and butene-1 were continuously fed in the reactor and polymerization was carried out. The polymerization conditions were set to the total pressure of 800 kg/cm$^2$G and the concentration of butene-1 of 45.9% by mol. Dimethylsilyl (tetramethylcyclopentadienyl)(3-tert-butyl-5-methyl-2-phenoxy)titanium dichloride was dissolved (0.066 µmol/g) in a mixed solution (a volume ratio of heptane: liquid paraffin=1:4) of heptane and liquid paraffin (Crystol 202, manufactured by Esso Sekiyu K.K.) and N,N-dimethylaniliniumtetrakis (pentafluorophenyl)borate (obtained by atomizing according to a re-precipitation method using toluene and heptane, the particle size is from 2 to 3 µm and particles having the particle size of not less than 10 µm are not observed) was dispersed (0.4 µmol/g) in the solution. Furthermore, the resulting suspension was adjusted so that a molar ratio of boron atom to Ti atom becomes 6.0. This mixed suspension and a heptane solution (5.47 µmol/g) of triisobutylaluminum were prepared in separate vessels, and the respective solutions were continuously fed in the reactor through a pipeline having a diameter of 3.175 mm at a feeding rate of 323 g/hour and 240 g/hour, respectively. The polymerization reaction temperature was set to 205° C. and a molar ratio of Al atom to Ti atom was set to 61.7. As a result, an ethylene-butene-1 copolymer having a density (without annealing) of 0.873 g/cm$^3$, MFR of 6.8 g/10 min., a molecular weight (Mw) of 72000 and a molecular weight distribution (Mw/Mn) of 1.7 was produced in a rate of 98.4 ton per one hour per mol of Ti atom.

Example 20

Using an autoclave type reactor having an internal volume of 1 liter, equipped with a stirring blade, ethylene and butene-1 were continuously fed in the reactor and polymerization was carried out. The polymerization conditions were set to a total pressure of 800 kg/cm$^2$G and a concentration of butene-1 of 47.0% by mol. Dimethylsilyl (tetramethylcyclopentadienyl)(3-tert-butyl-5-methyl-2-phenoxy)titanium dichloride was dissolved (0.066 µmol/g) in a mixed solution (a volume ratio of heptane:liquid paraffin=1:4) of heptane and liquid paraffin (Crystol 202, manufactured by Esso Sekiyu K.K.) and N,N-dimethylaniliniumtetrakis (pentafluorophenyl)borate (obtained by atomizing according to a re-precipitation method using toluene and heptane, the particle size is from 2 to 3 µm and particles having the particle size of not less than 10 µm are not observed) was dispersed (0.4 µmol/g) in the solution. Furthermore, the resulting suspension was adjusted so that a molar ratio of boron atom to Ti atom becomes 6.0. This mixed suspension and a heptane solution (5.47 µmol/g) of triisobutylaluminum were prepared in separate vessels, and the respective ones were continuously fed in the reactor at a feeding rate of 373 g/hour and 283 g/hour, respectively. The polymerization reaction temperature was set to 206° C. and a molar ratio of Al atom to Ti atom was set to 63.3. As a result, an ethylene-butene-1 copolymer having a density (no annealing) of 0.867 g/cm$^3$, a melting point of 42.6° C. and a MFR of 11.8 g/10 min. was produced in a rate of 106.3 ton per one hour per mol of Ti atom.

Example 21

Using an autoclave type reactor having an internal volume of 1 liter, equipped with a stirring blade, ethylene and butene-1 were continuously fed in a reactor and polymerization was performed. The polymerization conditions were set to a total pressure of 800 kg/cm$^2$G and a concentration of butene-1 of 43.9% by mol. Dimethylsilyl (tetramethylcyclopentadienyl)(3-tert-butyl-5-methyl-2-phenoxy)titanium dichloride was dissolved (0.066 µmol/g) in a mixed solution (a volume ratio of heptane:liquid paraffin=1:4) of heptane and liquid paraffin (Crystol 202, manufactured by Esso Sekiyu K.K.) and N,N-dimethylaniliniumtetrakis (pentafluorophenyl)borate (obtained by atomizing according to a re-precipitation method using toluene and heptane, the particle size is from 2 to 3 µm and particles having the particle size of not less than 10 µm are not observed) was dispersed (0.4 µmol/g) in the solution. Furthermore, the resulting suspension was adjusted so that a molar ratio of boron atom to Ti atom becomes 6.0. This mixed suspension and a heptane solution (5.47 µmol/g) of triisobutylaluminum were prepared in separate vessels, and the respective ones were continuously fed in the reactor at a feeding rate of 290 g/hour and 270 g/hour, respectively. The polymerization reaction temperature was set to 205° C. and a molar ratio of boron atom to Ti atom was set to 77.2. As a result, an ethylene-butene-1 copolymer having a MFR of 13.3 g/10 min. was produced in a rate of 104.5 ton per one hour per mol of Ti atom.

Example 22

Using an autoclave type reactor having an internal volume of 1 liter, equipped with a stirring blade, ethylene and hexene-1 were continuously fed in a reactor and polymerization was performed. Regarding the polymerization conditions, the total pressure was set to 796 kg/cm$^2$G and the concentration of hexene-1 was set to 30.8% by mol. A heptane solution obtained by mixing dimethylsilyl (tetramethylcyclopentadienyl)(3-tert-butyl-5-methyl-2-phenoxy)titanium dichloride and triisobutylaluminum (the concentration of the complex and that of triisobutylaluminum are 0.37 µmol/g and 18.5 µmol/g, respectively, and Al/Ti=50 mol/mol) and a toluene solution (1.85 µmol/g) of triphenylmethyltetrakis(pentafluorophenyl)borate were prepared in separate vessels, and the respective solutions were continuously fed in the reactor at a feeding rate of 260 g/hour and 425 g/hour, respectively. The polymerization reaction temperature was set to 200° C. and a molar ratio of boron atom to Ti atom was set to 8.2. As a result, an ethylene-hexene-1 copolymer having MFR of 3.0, a density (without annealing) of 0.887, a melting point of 63.9° C. and SCB of 34.8 was produced in a rate of 19.2 ton per one hour per mol of Ti atom.

Example 23

Using an autoclave type reactor having an internal volume of 1 liter, equipped with a stirring blade, ethylene and hexene-1 were continuously fed in a reactor and polymerization was performed. The polymerization conditions were set to a total pressure of 796 kg/cm$^2$G and a concentration of hexene-1 of 29.7% by mol. A heptane solution obtained by mixing dimethylsilyl (tetramethylcyclopentadienyl)(3-tert-butyl-5-methyl-2-phenoxy)titanium dichloride and triisobutylaluminum (the concentrations of the complex and triisobutylaluminum are 0.37 $\mu$mol/g and 18.5 $\mu$mol/g, respectively, and a molar ratio of Al atom to Ti atom is 50) and a suspension liquor (0.71 $\mu$mol/g) of N,N-dimethylaniliniumtetrakis(pentafluorophenyl)borate (a maximum particle diameter of 20 $\mu$m or less) atomized by wet pulverization, suspended in a mixed liquor (a volume ratio of heptane:liquid paraffin=1:4) of heptane and liquid paraffin (Crystol 202, manufactured by Esso Sekiyu K.K.), were prepared in separate vessels, and the respective solutions were continuously fed in the reactor at a feeding rate of 246 g/hour and 484 g/hour, respectively. The polymerization temperature was set to 210° C. and a molar ratio of boron atom to Ti atom was set to 3.6. As a result, an ethylene-hexene-1 copolymer having a MFR of 3.8 g/10 min. and a density (without annealing) of 0.889 g/cm$^3$ was produced in a rate of 28 ton per one hour per mol of Ti atom.

Example 24

Using an autoclave type reactor having an internal volume of 1 liter, equipped with a stirring blade, ethylene and hexene-1 were continuously fed in a reactor and polymerization was carried out. The polymerization conditions were set to a total pressure was set to 796 kg/cm$^2$G and a concentration of hexene-1 of 31.6% by mol. A heptane solution obtained by mixing dimethylsilyl (tetramethylcyclopentadienyl)(3-tert-butyl-5-methyl-2-phenoxy)titanium dichloride and triisobutylaluminum (the concentrations of the complex and triisobutylaluminum are 2 $\mu$mol/g and 200 $\mu$mol/g, respectively, and a molar ratio of Al atom to Ti atom is 100) and a liquid paraffin (a mixture of Crystol 202(130 cp at 18° C.) manufactured by Esso Sekiyu K.K.: IP Solvent 2028(3.2 cp at 19° C.) manufactured by Idemitsu Petrochemical Co., Ltd.=60:40 (% by volume)) suspension liquor (7.0 $\mu$mol/g) of N,N-dimethylaniliniumtetrakis (pentafluorophenyl)borate atomized by wet pulverization (maximum particle diameter: not more than 20 $\mu$m) were prepared in separate vessels, and the respective ones were continuously fed in the reactor at a feeding rate of 90 g/hour and 195 g/our, respectively. The polymerization temperature was set to 220° C. and the molar ratio of boron atom to Ti atom was set to 7.6. As a result, an ethylene-hexene-1 copolymer having a MFR of 5.8 g/10 min., a density (without annealing) of 0.888 g/cm$^3$, a melting point of 69.8° C. and SCB of 32.6 was produced in a rate of 11 ton per one hour per mol of Ti atom.

Example 25

Using an autoclave type reactor having an internal volume of 1 liter, equipped with a stirring blade, ethylene and hexene-1 were continuously fed in a reactor and polymerization was carried out. The polymerization conditions were set to a total pressure of 796 kg/cm$^2$G and a concentration of hexene-1 of 31.1% by mol. A heptane solution obtained by mixing dimethylsilyl (tetramethylcyclopentadienyl)(3-tert-butyl-5-methyl-2-phenoxy)titanium dichloride and triisobutylaluminum (the concentration of the complex and that of triisobutylaluminum are 0.37 $\mu$mol/g and 18.5 $\mu$mol/g, respectively, and the molar ratio of Al atom to Ti atom is 50) and a liquid paraffin (a mixture of Crystol 202 manufactured by Esso Sekiyu K.K.: IP Solvent 2028 manufactured by Idemitsu Petrochemical Co., Ltd.=60:40 (% by volume)) suspension liquor (1.39 $\mu$mol/g) of N,N-dimethylaniliniumtetrakis(pentafluorophenyl)borate atomized by wet grinding (maximum particle diameter: not more than 20 $\mu$m) in a mixed solution were prepared in separate vessels, and the respective ones were continuously fed in the reactor through a pipeline having a diameter of 3.175 mm at a feeding rate of 745 g/hour and 1235 g/hour, respectively. The polymerization temperature was set to 247° C. and the molar ratio of boron atom to Ti atom was set to 6.22. As a result, an ethylene-hexene-1 copolymer having a MFR of 55 g/10 min. and a density (without annealing) of 0.886 g/cm$^3$ was produced in a rate of 13 ton per one hour per mol of Ti atom.

As described above, according to the present invention, there is provided a method for efficiently producing an olefin polymer having narrow composition distribution, high molecular weight and arbitrary density, particularly a linear low-density polyethylene under the conditions of high temperature and high pressure by using a highly active catalyst containing a novel metallocene complex.

Example 26

100 Parts by weight of the ethylene-hexene-1 copolymer produced in Example 4 was mixed with 0.10 parts by weight of an antioxidant (Sumilizer BP76, manufactured by Sumitomo Chemical Co., Ltd.), 0.10 parts by weight of an antioxidant (Sandostab P-EPQ, manufactured by Sandoz Japan Co., Ltd) and 0.05 parts by weight of Hydrotalcite DHT-4A (manufactured by Kyowa Chemical Industry Co., Ltd.) by using a single screw extruder, and a film was formed by using the mixture.

The physical properties of the resulting copolymer and evaluation results of the film are shown in Table 1. And, FIG. 1 is a drawing showing a relation between the melt flow rate (MFR) and the intrinsic viscosity [$\eta$] measured in tetralin at 135° C. in the olefin copolymers used in the Examples and Comparative Example.

Comparative Example 1

Using a commercially available ethylene-butene-1 copolymer (Esprene SPO N0352, manufactured by Sumitomo Chemical Co., Ltd.) produced by solution polymerization in the presence of a vanadium catalyst, a film was formed in the same manner as in Example 26.

The results are shown in Table 1. As the result, the transparency of the resulting film was not satisfactory in comparison with Example 26.

Example 27

Using the ethylene-hexene-1 copolymer produced in Example 7, a film was obtained in the same manner as in Example 26.

The physical properties of the resulting copolymer and evaluation results of the film are shown in Table 1.

Comparative Example 2

Using an autoclave type reactor having an internal volume of 1 liter, equipped with a stirring blade, ethylene and hexene-1 were continuously fed in a reactor and polymerization was performed. Regarding the polymerization conditions, the total pressure was set to 800 kg/cm²G and the concentration of hexene-1 was set to 66.0% by mol. A toluene solution (0.1 g mol/g) of bis(n-butylcyclopentadienyl)zirconium dichloride manufactured by Witco Co. as a transition metal complex, a heptane solution (9.05 µmol/g) of triisobutylaluminum and a toluene solution (0.45 µmol/g) of N,N-dimethylaniliniumtetrakis(pentafluorophenyl)borate were prepared in separate vessels, and the respective solutions were continuously fed in the reactor, respectively. The polymerization temperature was set to 200° C., a molar ratio of Al atom to Zr atom was set to 63, and a molar ratio of Al atom to Ti atom was set to 4.4.

The results of the polymerization are shown in Table 1. Since the resulting copolymer had considerably high NMR, a film could not be produced.

TABLE 1

| | MFR (g/10 min) | [η] (dl/g) | Density (after annealing) (g/cm³) | Film thickness (µ) | Film Haze (%) | Tear strength (kg/cm) MD direction | Tear strength (kg/cm) TD direction |
|---|---|---|---|---|---|---|---|
| Example 26 | 1.7 | 1.4 | 0.901 | 30 | 2.4 | 60 | 100 |
| | | | | 80 | 2.8 | — | — |
| Comparative example 1 | 1.8 | 1.5 | 0.905 | 30 | 3.1 | 30 | 60 |
| | | | | 80 | 4.4 | — | — |
| Example 27 | 1.5 | 1.5 | 0.913 | 30 | 3.0 | 80 | 14- |
| | | | | 80 | 4.0 | — | — |
| Comparative example 2 | Impossible to measure because of too high value | | 0.924 | Impossible to produce a film | | | |

Industrial Applicability

As described in detail above, according to the present invention, there can be provided a novel olefin polymer having good transparency and strength characteristics.

The present invention can also provide a film or sheet of the above polyolefin polymer, which has good transparency and strength characteristics.

Furthermore, according to the present invention, there can be provided a method for efficiently producing an olefin polymer having a narrow composition distribution, high molecular weight and an optional density, particularly a linear low-density polyethylene, by using a highly active catalyst containing a novel metallocene complex.

What is claimed is:

1. A method for producing an olefin polymer, comprising the step of homopolymerizing an olefin or copolymerizing two or more olefins at a temperature of at least 130° C. under a pressure of at least 300 kg/cm²G with a catalyst for olefin polymerization, comprising the following (A), (B) and (C); (A) and (B); or (A) and (C):

(A) a transition metal complex represented by the following general formula (I):

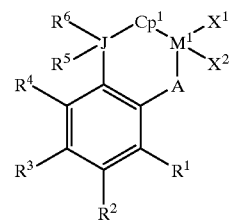

wherein $M^1$ represents a transition metal atom of Group IV of the Periodic Table of the Elements; A represents an atom of Group XVI of the Periodic Table of the Elements; J represents an atom of Group XIV of the Periodic Table of the Elements; $Cp^1$ represents a group having a cyclopentadiene anion skeleton; $X^1$, $X^2$, $R^1$, $R^2$, $R^3$, $R^4$, $R^5$ and $R^6$ independently represent a hydrogen atom, a halogen atom, an alkyl group, an aralkyl group, an aryl group, a substituted silyl group, an alkoxy group, an aralkyloxy group, an aryloxy group or a di-substituted amino group; and $R^1$, $R^2$, $R^3$, $R^4$, $R^5$ and $R^6$ may be optionally combined with each other to form a ring;

(B) at least one aluminum compound selected from the following (B1) to (B3):

(B1) an organoaluminum compound represented by the general formula $E^1_a AlZ_{3-a}$;

(B2) a cyclic aluminoxane having a structure represented by the general formula $(Al(E^2)\text{—}O\text{—})_b$; and (B3) a linear aluminoaxe having a structure represented by the general formula $E^3(\text{—}Al(E^3)\text{—}O\text{—})_c AlE^3_2$, wherein $E^1$, $E^2$ an $E^3$ respectively represents a hydrocarbon group, all of $E^1$, $E^2$ and $E^3$ may be the same or different, Z represents a hydrogen atom or a halogen atom, and all of Z may be the same or different, a represents a numeral of 0 to 3, b represents an integer of not less than 2, and c represents an integer of not less than 1, and (C) a boron compound of any one of the following (C1) to (C3):

(C1) a boron compound represented by the general formula $BQ^1Q^2Q^3$;

(C2) a boron compound represented by the general formula $G^+(BQ^1Q^2Q^3Q^4)^-$; and (C3) a boron compound represented by the general formula $(L\text{—}H)^+(BQ^1Q^2Q^3Q^4)^-$, wherein B represents a boron atom in the trivalent valence state, $Q^1$ to $Q^4$ may be the same or different and represent a halogen atom, a hydrocarbon group, a halogenated hydrocarbon group, a substituted silyl group, an alkoxy group or a di-substituted amino group, $G^+$ represents an inorganic or organic cation, L represents a neutral Lewis base, and $(L\text{—}H)^+$ represents a Brønsted acid.

2. The method for producing an olefin polymer according claim 1, wherein the pressure is from 350 to 3500 kg/cm²G.

3. The method for producing an olefin polymer according claim 1 or 2, wherein the temperature is from 135 to 350° C.

4. The method for producing an olefin polymer according to claim 1, wherein $R^1$ in the general formula (I) is an oxygen atom.

5. The method for producing an olefin polymer according to claim 1, wherein $R^1$ in the general formula (I) is an alkyl group, an aralkyl group, an aryl group or a substituted silyl group.

6. The method for producing an olefin polymer according to claim 1, wherein each of $X^1$ and $X^2$ in the general formula (I) is independently a halogen atom, alkyl group, an aralkyl group, an alkoxy group, an aryloxy group or a di-substituted amino group.

7. The method for producing an olefin polymer according to claim 1, wherein the compound (B) is triethylaluminum, triisobutylaluminum or methylaluminoxane.

8. The method for producing an olefin polymer according to claim 1, wherein the compound (C) is dimethylaniliniumtetrakis(pentafluorophenyl)borate or triphenylmethyltetrakis(pentafluorophenyl)borate.

9. The method for producing an olefin polymer according to claim 1, wherein the catalyst for olefin polymerization is a catalyst for olefin polymerization, comprising:

(A) and (B2), or (A and (B3).

10. The method for producing an olefin polymer according to claim 1, wherein the catalyst for olefin polymerization is a catalyst for olefin polymerization comprising (A), (B) and (C).

11. The method for producing an olefin polymer according to claim 1, wherein the olefin polymer is a copolymer of ethylene and an α-olefin.

12. An olefin polymer obtained by the method for producing an olefin polymer of claim 1.

13. An olefin polymer having (A) a density of from 0.0850 to 0.940 g/cm$^3$, (B) a melt flow rate (MFR) of from 0.1 to 200 g/10 minutes, and (C) a relation between the melt flow rate (MFR) and an intrinsic viscosity ($\mu$) measured in tetralin at 135° C. satisfying the condition of the following equation (1):

$$-4.04 \log (\mu)+0.6 \leq \log \text{MFR} \leq -4.04 \log (\mu)+0.96 \qquad (1).$$

14. The olefin polymer according to claim 13, wherein (C) the relation between the melt flow rate (MFR) and an intrinsic viscosity measured in tetralin at 135° C. satisfies the condition of the following equation 2:

$$-4.04 \log (\mu)+0.76 \leq \log \text{MFR} \leq -4.04 \log (\mu)+0.96 \qquad (2).$$

15. The olefin polymer according to claim 13 or 14, which is an olefin polymer obtained by polymerizing in the presence of a metallocene catalyst.

16. The olefin polymer according to claim 13 or 14, which is an olefin polymer obtained by polymerizing one or two olefins.

17. The olefin polymer according to claim 13 or 14, wherein an olefin polymer is obtained by homopolymerizing an olefin or copolymerizing two or more olefins at a temperature of at least 130° C. under a pressure of at least 300 kg/cm$^2$G.

18. A film or sheet characterized by comprising the olefin polymer of claim 13 or 14.

* * * * *